(12) United States Patent
Winslow et al.

(10) Patent No.: US 7,524,324 B2
(45) Date of Patent: Apr. 28, 2009

(54) SYSTEM AND METHOD FOR AN INTERSPINOUS PROCESS IMPLANT AS A SUPPLEMENT TO A SPINE STABILIZATION IMPLANT

(75) Inventors: Charles J. Winslow, Walnut Creek, CA (US); Steve Mitchell, Pleasant Hill, CA (US)

(73) Assignee: Kyphon SARL, Neuchatel (CH)

( * ) Notice: Subject to any disclaimer, the term of this patent is extended or adjusted under 35 U.S.C. 154(b) by 482 days.

(21) Appl. No.: 11/003,091

(22) Filed: Dec. 3, 2004

(65) Prior Publication Data

US 2005/0245929 A1  Nov. 3, 2005

Related U.S. Application Data

(60) Provisional application No. 60/565,971, filed on Apr. 28, 2004.

(51) Int. Cl.
*A61B 17/70* (2006.01)
*A61B 17/88* (2006.01)

(52) U.S. Cl. .................. 606/248; 606/60; 606/246; 606/279

(58) Field of Classification Search .............. 623/16.11, 623/17.11–17.16; 606/60, 246, 248–252, 606/263, 279
See application file for complete search history.

(56) References Cited

U.S. PATENT DOCUMENTS

| | | | |
|---|---|---|---|
| 2,456,806 A | 12/1948 | Wolffe | |
| 2,677,369 A | 5/1954 | Knowles | |
| 3,426,364 A | 2/1969 | Lumb | |
| 3,643,658 A | 2/1972 | Steinemenan | |
| 3,648,691 A | 3/1972 | Lumb | |
| 3,867,728 A | 2/1975 | Stubstad | |
| 3,875,595 A | 4/1975 | Froning | |
| 4,034,418 A | 7/1977 | Jackson | |
| 4,219,015 A | 8/1980 | Steinemenan | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,455,690 A | 6/1984 | Homsy | |

(Continued)

FOREIGN PATENT DOCUMENTS

CA  2015507  1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Eduardo C Robert
*Assistant Examiner*—Tara R George
(74) *Attorney, Agent, or Firm*—Coats & Bennett, P.L.L.C.

(57) ABSTRACT

An implant is used to distract and maintain the distraction of spinous processes of adjacent vertebrae of the spine. The implant can be secured to a spine stabilization system. The combination of the spine stabilization system with spine distraction provides an improved therapeutic benefit to the patient receiving such an implant.

7 Claims, 23 Drawing Sheets

U.S. PATENT DOCUMENTS

| | | | |
|---|---|---|---|
| 4,479,491 A | 10/1984 | Martin | |
| 4,501,269 A | 2/1985 | Bagby | |
| 4,502,161 A | 3/1985 | Wall | |
| 4,553,273 A | 11/1985 | Wu | |
| 4,554,914 A | 11/1985 | Kapp | |
| 4,599,084 A | 7/1986 | Nashef | |
| 4,599,086 A | 7/1986 | Doty | |
| 4,604,995 A | 8/1986 | Stephens | 128/69 |
| 4,611,582 A | 9/1986 | Duff | 128/69 |
| 4,636,217 A | 1/1987 | Ogilvie | 623/17 |
| 4,643,178 A | 2/1987 | Nastari | 128/92 |
| 4,657,550 A | 4/1987 | Daher | 623/17 |
| 4,685,447 A | 8/1987 | Iversen | 128/1 R |
| 4,696,290 A | 9/1987 | Steffee | 128/69 |
| 4,714,469 A | 12/1987 | Kenna | 623/17 |
| 4,743,256 A | 5/1988 | Brantigan | 623/17 |
| 4,772,287 A | 9/1988 | Ray | 623/17 |
| 4,790,303 A | 12/1988 | Steffee | 128/924 M |
| 4,834,757 A | 5/1989 | Brantigan | 623/17 |
| 4,878,915 A | 11/1989 | Brantigan | 623/17 |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,923,471 A | 5/1990 | Morgan | 623/16 |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,888 A | 11/1990 | Scholten | 606/94 |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,180,381 A | 1/1993 | Aust | 606/61 |
| 5,192,327 A | 3/1993 | Brantigan | 623/17 |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,352,225 A | 10/1994 | Yuan | 606/61 |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,372 A | 3/1995 | Holt | 606/61 |
| 5,415,661 A | 5/1995 | Holmes | 606/69 |
| 5,437,672 A | 8/1995 | Alleyne | 606/61 |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A * | 3/1996 | Howland et al. | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,736 A | 10/1996 | Ray | 623/17 |
| 5,571,191 A | 11/1996 | Fitz | 623/17 |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,658,286 A | 8/1997 | Sava | 606/61 |
| 5,672,177 A | 9/1997 | Seldin | 606/71 |
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,702,455 A | 12/1997 | Saggar | 623/17 |
| 5,725,582 A | 3/1998 | Bevan | 623/17 |
| 5,741,261 A | 4/1998 | Moskovitz | 606/79 |
| 5,766,251 A | 6/1998 | Koshino | 623/16 |
| 5,766,252 A | 6/1998 | Henry | 623/17 |
| 5,800,438 A | 9/1998 | Tuke | 606/90 |
| 5,824,098 A | 10/1998 | Stein | 623/20 |
| 5,836,948 A | 11/1998 | Zucherman | 606/61 |
| 5,860,977 A | 1/1999 | Zucherman | 606/61 |
| 5,865,846 A | 2/1999 | Bryan | 623/17 |
| 5,876,402 A | 3/1999 | Errico | 606/61 |
| 5,876,404 A | 3/1999 | Zucherman | 606/61 |
| 5,879,396 A | 3/1999 | Walston | 623/21 |
| 5,885,299 A | 3/1999 | Winslow | 606/99 |
| 5,888,224 A | 3/1999 | Beckers | 627/17 |
| 5,888,226 A | 3/1999 | Rogozinski | 623/17 |
| 5,951,555 A | 9/1999 | Rehak | 606/61 |
| 5,976,186 A | 11/1999 | Bao | 623/17 |
| 6,001,130 A | 12/1999 | Bryan | 623/17 |
| 6,022,376 A | 2/2000 | Assell | 623/17 |
| 6,030,162 A | 2/2000 | Huebner | 411/413 |
| 6,045,554 A | 4/2000 | Grooms | 606/73 |
| 6,048,204 A | 4/2000 | Klardie | 433/174 |
| 6,048,342 A | 4/2000 | Zucherman | 606/61 |
| 6,048,344 A | 4/2000 | Schenk | 606/73 |
| 6,068,630 A | 5/2000 | Zucherman | 606/61 |
| RE36,758 E | 6/2000 | Fitz | |
| 6,099,531 A | 8/2000 | Bonutti | 606/87 |
| 6,113,639 A | 9/2000 | Ray | 623/17.16 |
| 6,129,730 A | 10/2000 | Bono | 606/73 |
| 6,132,464 A | 10/2000 | Martin | 623/17 |
| 6,139,550 A | 10/2000 | Michelson | 606/69 |
| 6,152,927 A | 11/2000 | Farris | 606/69 |
| 6,156,067 A | 12/2000 | Bryan | 623/17.15 |
| 6,190,414 B1 | 2/2001 | Young | 623/17.15 |

| Patent Number | Date | Name | Class |
|---|---|---|---|
| 6,193,721 B1 | 2/2001 | Michelson | 606/70 |
| 6,200,322 B1 | 3/2001 | Branch | 606/96 |
| 6,206,922 B1 | 3/2001 | Zdeblick | 623/17.11 |
| 6,217,580 B1 | 4/2001 | Levin | 606/71 |
| 6,224,602 B1 | 5/2001 | Hayes | 606/69 |
| 6,224,607 B1 | 5/2001 | Michelson | 606/96 |
| 6,228,900 B1 | 5/2001 | Shen | 522/153 |
| 6,234,705 B1 | 5/2001 | Troxell | 403/237 |
| 6,235,030 B1 * | 5/2001 | Zucherman et al. | 606/61 |
| 6,261,296 B1 | 7/2001 | Aebi | 606/90 |
| 6,293,949 B1 | 9/2001 | Justis | 606/61 |
| 6,306,136 B1 | 10/2001 | Baccelli | 606/61 |
| 6,352,537 B1 | 3/2002 | Strnad | 606/61 |
| 6,368,351 B1 | 4/2002 | Glenn | 623/17.15 |
| 6,383,186 B1 | 5/2002 | Michelson | 606/69 |
| 6,395,030 B1 | 5/2002 | Songer | 623/17.11 |
| 6,398,783 B1 | 6/2002 | Michelson | 606/70 |
| 6,402,756 B1 | 6/2002 | Ralph | 606/71 |
| 6,419,703 B1 | 7/2002 | Fallin | 623/17.11 |
| 6,428,542 B1 | 8/2002 | Michelson | 606/70 |
| 6,436,145 B1 | 8/2002 | Miller | 623/20.34 |
| 6,440,169 B1 * | 8/2002 | Elberg et al. | 623/17.16 |
| 6,454,771 B1 | 9/2002 | Michelson | 606/70 |
| 6,458,131 B1 | 10/2002 | Ray | 606/61 |
| 6,527,776 B1 | 3/2003 | Michelson | 606/70 |
| 6,558,423 B1 | 5/2003 | Michelson | 623/17.11 |
| 6,558,686 B1 | 5/2003 | Darouiche | 424/423 |
| 6,565,570 B2 | 5/2003 | Sterett | 606/69 |
| 6,565,605 B2 | 5/2003 | Goble | 623/17.11 |
| 6,579,318 B2 * | 6/2003 | Varga et al. | 623/17.11 |
| 6,579,319 B2 | 6/2003 | Goble | 623/17.11 |
| 6,582,437 B2 | 6/2003 | Dorchak | 606/90 |
| 6,592,586 B1 | 7/2003 | Michelson | 606/71 |
| 6,610,091 B1 | 8/2003 | Reiley | 623/17.11 |
| 6,620,163 B1 | 9/2003 | Michelson | 606/61 |
| 6,626,944 B1 * | 9/2003 | Taylor | 623/17.16 |
| 6,669,729 B2 | 12/2003 | Chin | 623/17.11 |
| 6,699,246 B2 | 3/2004 | Zucherman et al. | |
| 6,712,852 B1 | 3/2004 | Chung | 623/17.11 |
| 6,730,127 B2 | 5/2004 | Michelson | 623/17.16 |
| 6,752,831 B2 | 6/2004 | Sybert | 623/13.17 |
| 6,755,841 B2 | 6/2004 | Fraser | 606/99 |
| 6,761,720 B1 | 7/2004 | Senegas | 606/61 |
| 6,783,527 B2 | 8/2004 | Drewry | 606/61 |
| 6,800,670 B2 | 10/2004 | Shen | 522/153 |
| 6,811,567 B2 | 11/2004 | Reiley | 623/17.11 |
| 2001/0012938 A1 | 8/2001 | Zucherman | |
| 2001/0018614 A1 | 8/2001 | Bianchi | |
| 2001/0037111 A1 * | 11/2001 | Dixon et al. | 606/61 |
| 2002/0004683 A1 | 1/2002 | Michelson | |
| 2002/0016595 A1 | 2/2002 | Michelson | |
| 2002/0022843 A1 | 2/2002 | Michelson | |
| 2002/0065557 A1 | 5/2002 | Goble | |
| 2002/0072800 A1 | 6/2002 | Goble | |
| 2002/0077700 A1 | 6/2002 | Varga | |
| 2002/0099376 A1 | 7/2002 | Michelson | |
| 2002/0128655 A1 | 9/2002 | Michelson | |
| 2002/0133155 A1 | 9/2002 | Ferree | |
| 2002/0151895 A1 | 10/2002 | Soboleski | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0004572 A1 | 1/2003 | Goble | |
| 2003/0028250 A1 | 2/2003 | Reiley | |
| 2003/0040746 A1 | 2/2003 | Mitchell | |
| 2003/0060828 A1 | 3/2003 | Michelson | |
| 2003/0078668 A1 | 4/2003 | Michelson | |
| 2003/0181912 A1 | 9/2003 | Michelson | |
| 2003/0191471 A1 | 10/2003 | Michelson | |
| 2003/0191472 A1 | 10/2003 | Michelson | |
| 2003/0191532 A1 | 10/2003 | Goble | |
| 2003/0204259 A1 | 10/2003 | Goble | |
| 2004/0006391 A1 | 1/2004 | Reiley | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0087948 A1 | 5/2004 | Suddaby | |
| 2004/0111154 A1 | 6/2004 | Reiley | |
| 2004/0116927 A1 | 6/2004 | Graf | |
| 2004/0122427 A1 | 6/2004 | Holmes | |
| 2004/0127989 A1 | 7/2004 | Dooris | |
| 2004/0143268 A1 | 7/2004 | Falahee | |
| 2004/0181226 A1 | 9/2004 | Michelson | |
| 2004/0181229 A1 | 9/2004 | Michelson | |
| 2004/0186475 A1 | 9/2004 | Falahee | |
| 2004/0186476 A1 | 9/2004 | Michelson | |
| 2004/0210313 A1 | 10/2004 | Michelson | |
| 2004/0210314 A1 | 10/2004 | Michelson | |
| 2004/0220678 A1 | 11/2004 | Chow | |
| 2004/0230201 A1 | 11/2004 | Yuan | |
| 2004/0230304 A1 | 11/2004 | Yuan | |
| 2004/0236334 A1 | 11/2004 | Michelson | |
| 2004/0236335 A1 | 11/2004 | Michelson | |
| 2005/0027297 A1 | 2/2005 | Michelson | |
| 2005/0027298 A1 | 2/2005 | Michelson | |
| 2005/0209603 A1 * | 9/2005 | Zucherman et al. | 606/90 |

FOREIGN PATENT DOCUMENTS

| | | |
|---|---|---|
| DE | 2821678 A1 | 4/1980 |
| DE | 3113142 A1 | 1/1982 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| JP | 10-179622 | 7/1998 |
| SU | 1484348 A1 | 6/1989 |
| WO | WO 90/00037 | 1/1990 |
| WO | WO 9004948 A1 * | 5/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |

| | | |
|---|---|---|
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 02/34120 A2 | 5/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Waldemar Link, brochure entitled *Wirbelsäulen-Chirurgie: Instrumentarium Und Implantate Zur Wirbelsäulen-Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

International Search Report dated Jan. 25, 2005.

International Search Report for PCT/US06/10521 (mailed Nov. 22, 2006).

* cited by examiner

SYSTEM AND METHOD FOR AN INTERSPINOUS PROCESS IMPLANT AS A SUPPLEMENT TO A SPINE STABILIZATION IMPLANT

PRIORITY CLAIM

This application claims priority to U.S. Provisional Application No. 60/565,971, entitled, "System and Method for an Interspinous Process Implant as a Supplement to a Spine Stabilization Implant," by Mitchell, S. et al., filed Apr. 28, 2004.

CROSS-REFERENCE TO RELATED APPLICATIONS

This application is related to U.S. patent application Ser. No. 10/230,505, entitled, "Deflectable Spacer for Use as an Interspinous Process Implant and Method," by Zucherman et al., filed Aug. 29, 2002.

This application is further related to U.S. patent application Ser. No. 10/037,236, entitled, "Inter-spinous Process Implant and Method with Deformable Spacer," by Zucherman et al., filed Nov. 9, 2001.

This application is also related to U.S. patent application Ser. No. 10/694,103, entitled, "Interspinous Process Implant with Radiolucent Spacer and Lead-In Tissue Expander," by Zucherman et al., filed Oct. 27, 2003.

FIELD OF THE INVENTION

This invention relates to an interspinous process implant to supplement a spine stabilization implant or other spine implant, and method for implantation.

BACKGROUND OF THE INVENTION

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs; (2) complex physiological motion between these parts; and (3) protection of the spinal cord and nerve roots.

As the present society ages, it is anticipated that there will be an increase in adverse spinal conditions which are characteristic of older people. By way of example, with aging comes an increase in spinal stenosis (including, but not limited to, central canal and lateral stenosis), and facet arthropathy. Spinal stenosis typically results from the thickening of the bones that make up the spinal column and is characterized by a reduction in the available space for the passage of blood vessels and nerves.

Pain associated with such stenosis and other ailments can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the spine. Such implants would distract, or increase the space between, the vertebrae to increase the foraminal area and reduce pressure on the nerves and blood vessels of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

DETAILED DESCRIPTION OF THE PREFERRED EMBODIMENTS OF THE INVENTION

Embodiments of the present invention relate to an interspinous process implant that, together with a spine stabilization system, further stabilizes the spine while distracting or maintaining the distraction of the spinous processes of two affected adjacent vertebrae. Generally speaking, the implant is used to limit extension in order to reduce or eliminate pain in the spine that is due to extension. Preferably the implant is flexible so as to cushion the load when the spinous processes come in contact with the implant. The implant can be appropriately sized to maintain a desired amount of distraction. The implant does not limit flexion.

More specifically, the embodiments of the present invention concern a distraction body that is inserted between adjacent spinous processes. The distraction body is adapted to anchor a first end of a first tether and a first end of a second tether. The second ends of each of these tethers are then secured to a spine stabilization system. The spine stabilization system comprises two components, a first component on the left lateral side of the spinous processes and a second component on the right lateral side of the spinous processes. The tethers can be artificial ligaments, and the spine stabilization system can incorporate pedicle screws to secure hardware and secondary screws or other anchors that secure the rods to the pedicles of the lumbar spine. Alternatively, other compatible bone anchors can be used.

Figure 1:
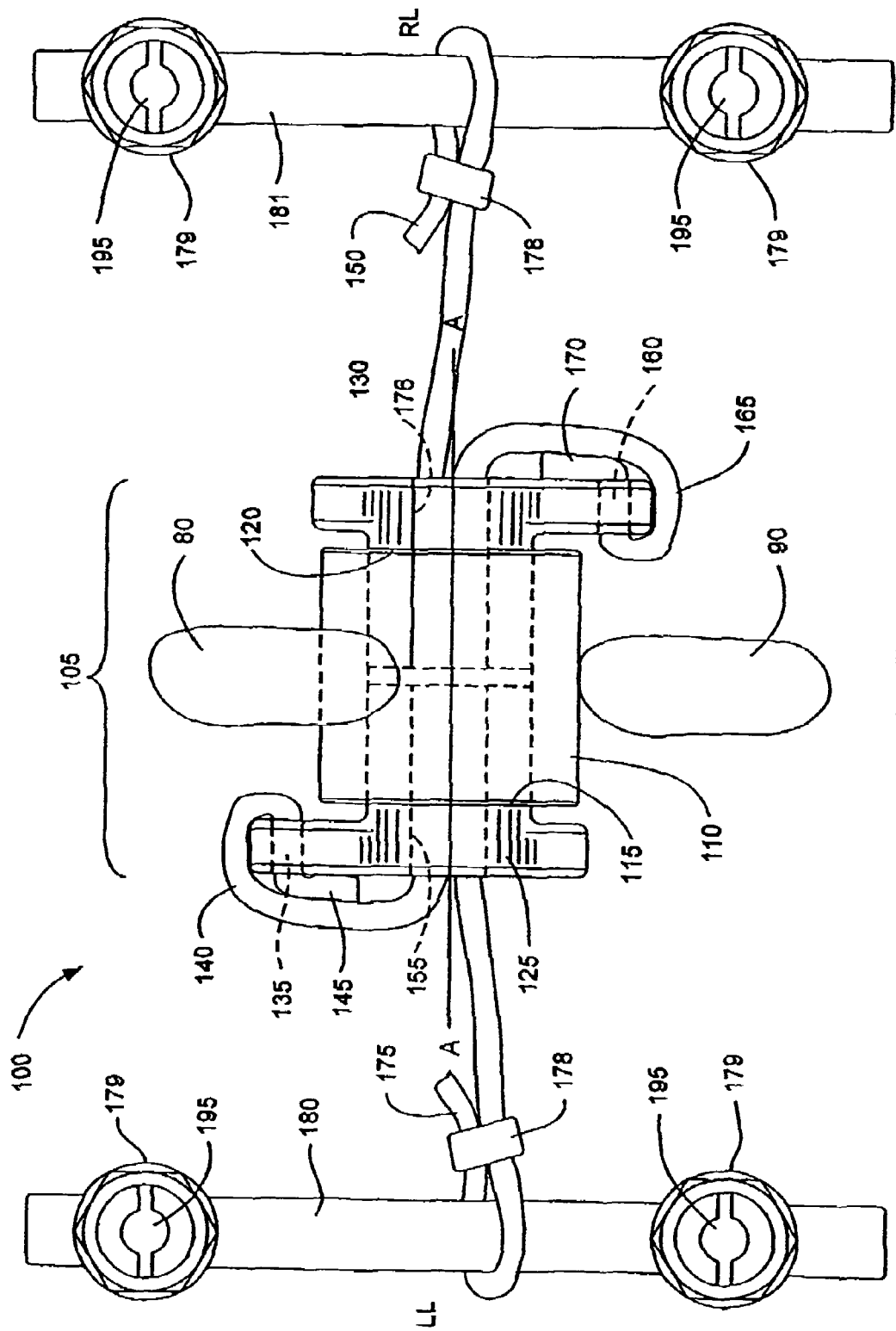
FIG. 1 is a posterior view of the distraction body, tethers, and spinal stabilization system of a disclosed embodiment of the invention, depicted as implanted in the spine.
Figure 2:
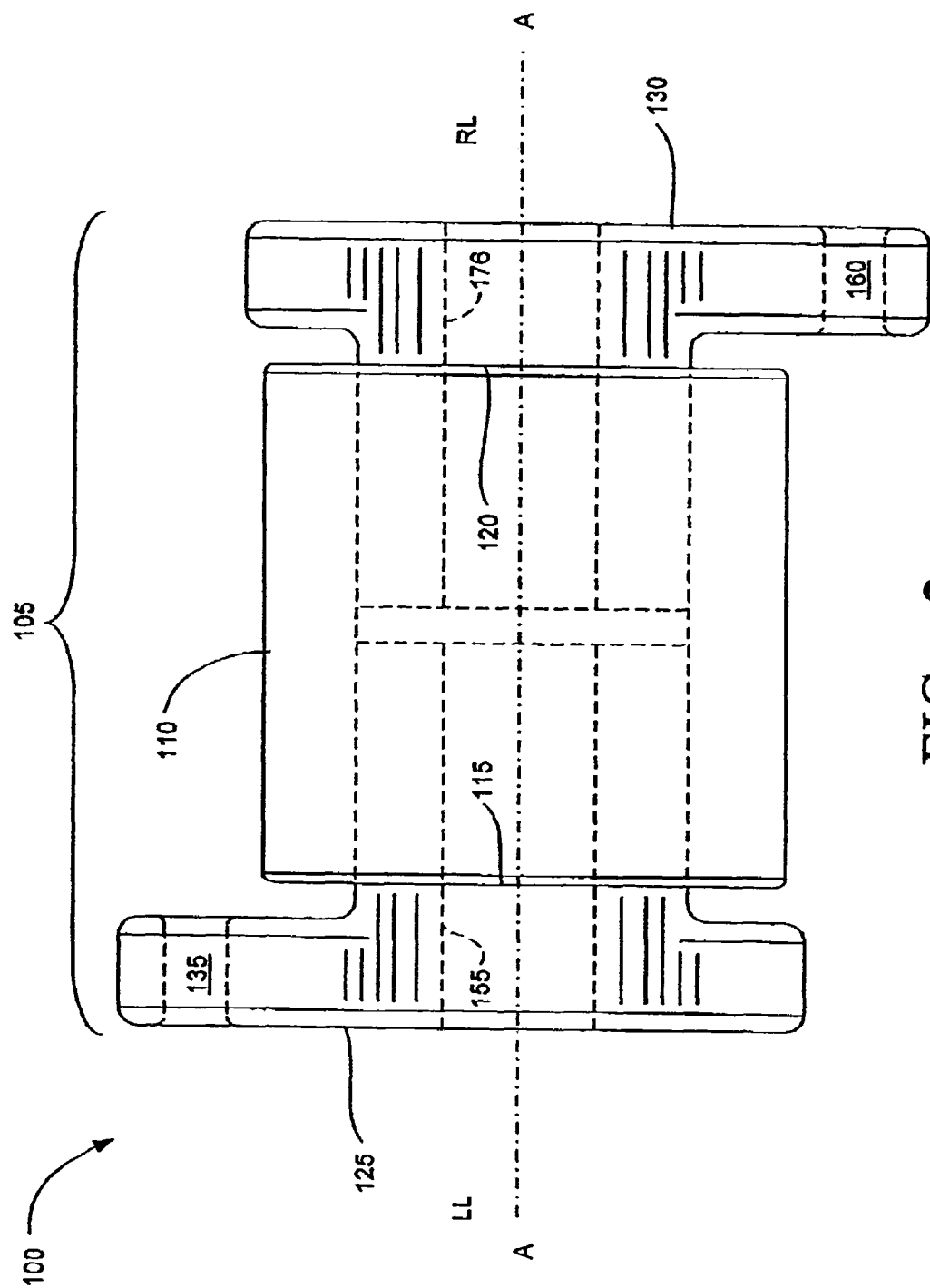
FIG. 2 is a side view of an embodiment of the distraction body of the disclosed invention, without tethers for an embodiment of the spine stabilization system of the disclosed implant of the invention.
Figure 3:
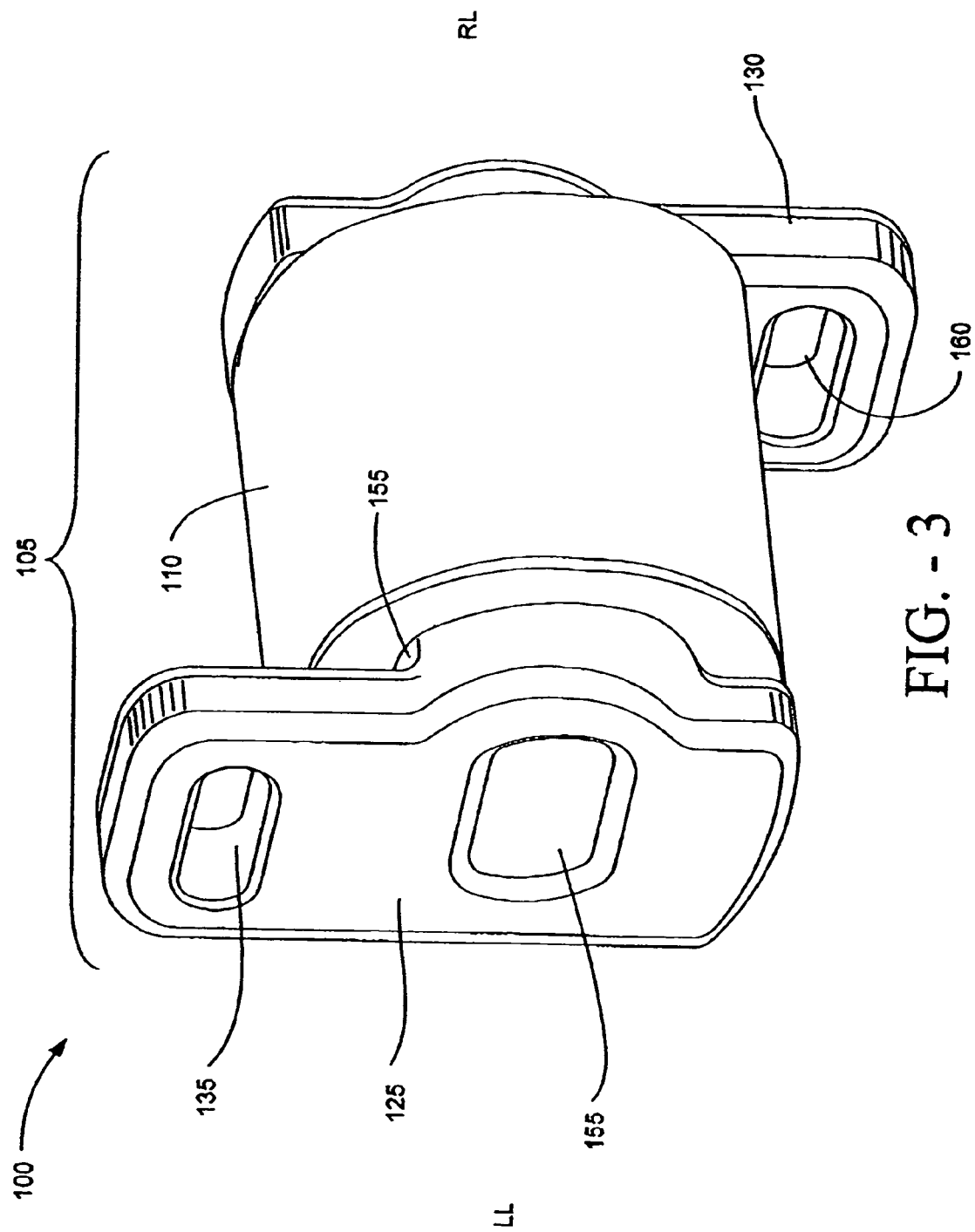
FIG. 3 is a perspective view of the embodiment of the distraction body of the implant of the disclosed invention depicted in FIGS. 1 and 2.
Figure 4:
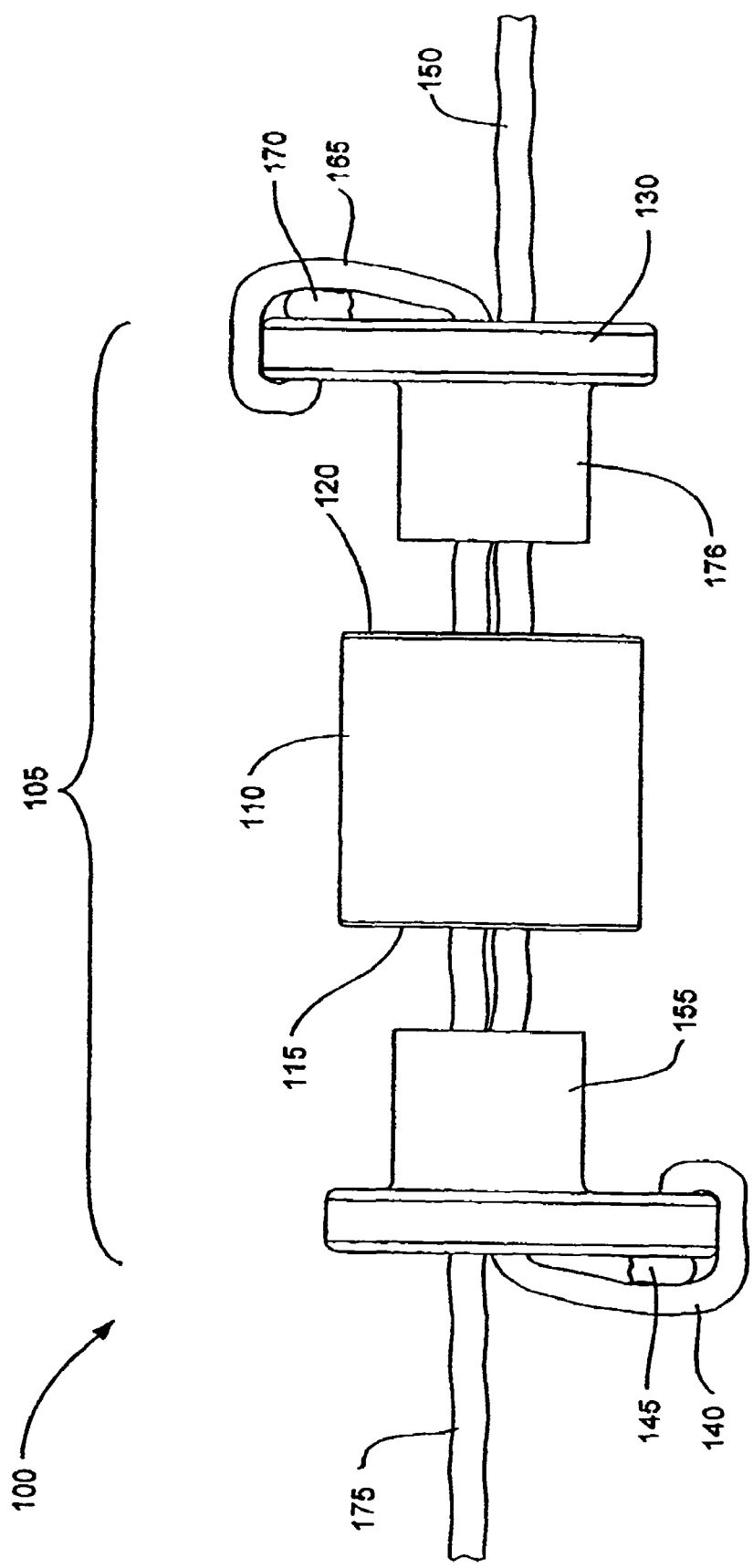
FIG. 4 is an exploded side view of the embodiment of the distraction body of an implant of the disclosed invention depicted in FIGS. 1-3, with tethers.

FIG. 1 shows an embodiment of the disclosed implant 100 of the invention, as implanted in the spine to distract the spinous processes of two adjacent vertebrae and to stabilize the affected spine. The implant 100 comprises a distraction body 105, which is implanted between the spinous processes of adjacent vertebrae. The distraction body 105 is comprised of a spacer 110 which fits between spinous processes 80, 90, and which includes a first open end 115 and a second open end 120, a first wing 125 which fits into the first open end 115 and a second wing 130 which fits into the second open end 120.

As can be seen in the figures and understood, the spacer 110 preferably is elliptical or oval in shape to better conform to the anatomy of the spine between spinous processes. Alternately, the spacer 110 can be round or have other cylindrical shapes. Preferably the spacer 110 has some flexibility in order to cushion the load with the spinous process come into contact with the spacer 110.

Implant 100 can be made of a number of materials including, by way of example only, medical implantable stainless steel or titanium. The implant may also be made of polymers. In this embodiment, the spacer is made out of a polymer which is a thermoplastic. One such polymer is a polyketone known as polyetheretherketone (PEEK™). More specifically, the material can be PEEK 450G, which is an unfilled PEEK approved for medical implantation available from Victrex of Lancashire, Great Britain. (Victrex is located at www-.matweb.com, or see Boedeker at www.boedeker.com). Other sources of this material include Gharda located in Panoli, India (www.ghardapolymers.com). The spacer 110 can be formed by extrusion, injection, compression molding and/or machining techniques. This material has appropriate physical and mechanical properties and is suitable for carrying and spreading the physical load between the spinous process. For example in this embodiment the PEEK has the following approximate properties:

| Density | 1.3 g/cc |
|---|---|
| Rockwell M | 99 |
| Rockwell R | 126 |
| Tensile Strength | 97 MPa |
| Modulus of Elasticity | 3.5 GPa |
| Flexural Modulus | 4.1 Gpa |

It should be noted that the material selected also can be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, the spacer 110 is manufactured from polyetheretherketone (PEEK™), available from Victrex. As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The spacer also can be comprised of polyetherketoneketone (PEKK).

Other material that can be used include polyetherketone (PEK), polyetherketoneetherketoneketone (PEKEKK), and polyetheretherketoneketone (PEEKK), and generally a polyaryletheretherketone. Other polyketones can be used, as well as other thermoplastics. The spacer also can be made of titanium.

Reference to appropriate polymers that can be used in the spacer can be made to the following documents, all of which are incorporated herein by reference. These documents include: U.S. patent applications Ser. Nos. 10/230,505; 10/037,236; and 10/694,103, which are incorporated herein by reference. The following cross-referenced applications are also incorporated by reference: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

The threading of a first tether 140 and a second tether 165 is viewed in detail in FIGS. 1-7. As depicted in FIGS. 2-7, each wing can have two bores. An outer bore on each wing is used to anchor a first end of each tether. An inner bore on each wing, which passes through the segment of the wing that fits inside the spacer 110, accommodates the unanchored second ends of two different tethers that pass each other through the spacer 110 in opposite directions.

Thus, the first wing 125 has a first outer bore 135 that is situated outside of the first open end 115 of the spacer 110. The first outerbore 135 anchors the first tether 140. That is, a first end 145 of the first tether 140 is secured to the first outer bore 135. A second end 150 of the first tether 140 is then passed through a first inner bore 155 of the first wing 125, first wing 125 which fits inside the first open end 115 of the spacer 110. The first tether 140 continues to be threaded through the spacer 110, through a second inner bore 176 of second wing 130, which second wing 130 fits inside the second open end 120 of the spacer 110, and to an exterior of the distraction body 105 on the opposite (i.e., right lateral) side from where the first tether 140 is anchored (i.e., left lateral).

Similarly, the second wing 130 has a second outer bore 160 located outside the second open end 120 of the spacer 110. A first end 170 of the second tether 165 is anchored to the second outer bore 160. A second end 175 of the second tether 165 is then passed through the second inner bore 176 of the second wing 130, which second wing 130 fits inside the second open end 120 of the spacer 110. The second tether 165 then passes through the spacer 110, and to the exterior of the distraction body 105 through the first inner bore 155 of the first wing 125.

With the tethers threaded and anchored as described, the second ends 150, 175 of the first and second tethers 140, 165 respectively, pass each other in opposite directions when threaded through the first inner bore 115, the spacer 110, and the second inner bore 176, while the first ends 145, 170 of the first and second tethers 140, 165 respectively, are anchored to the outer bores 135, 160.

The tethers 140, 165, can include artificial ligaments made from polyethylene tetraphthalate fibers or other appropriate biocompatible, flexible fibers. The tethers ensure that the distraction body 105 is not displaced from between the spinous processes of adjacent vertebrae.

As shown in FIGS. 1-7, the first and second wings 125, 130 depicted have first and second outer bores 135, 160. The outer bores 135, 160 in this embodiment are substantially parallel to an elongated axis A-A of the spacer 110. It is further within the scope of this disclosure of the invention to configure the first and second outer bores 135, 160 bent to create an "L"-shape, i.e., they can be bent at an angle with respect to the elongated axis A-A. For example, the first and second outer bores 135, 160 can be bent at an angle so that the axis of each outer bores 135, 160 is substantially perpendicular to the elongated axis A-A of the spacer 110, in this particular embodiment (FIGS. 8-11).

As mentioned above, the second ends 150, 175 of the first and second tethers 140, 165 respectively anchor the tethers to a spine stabilization system as described below. The first and second tethers 140, 165 can be secured to the spine stabilization system with a cuff or clip 178 made from a biocompatible material that is capable of grasping the tether material and preventing it from slipping. Alternatively, the tethers 140, 165 can be sewn, pierced, pinned, or tied to secure the tethers under tension to the spine stabilization system. The configuration of the distraction body 105 tethered to the spine stabilization system prevents displacement of the distraction body 105 from position between adjacent spinous processes. The combination of the spine stabilization system with spine distraction provides an improved therapeutic benefit to the patient receiving such implant.

Figure 16:
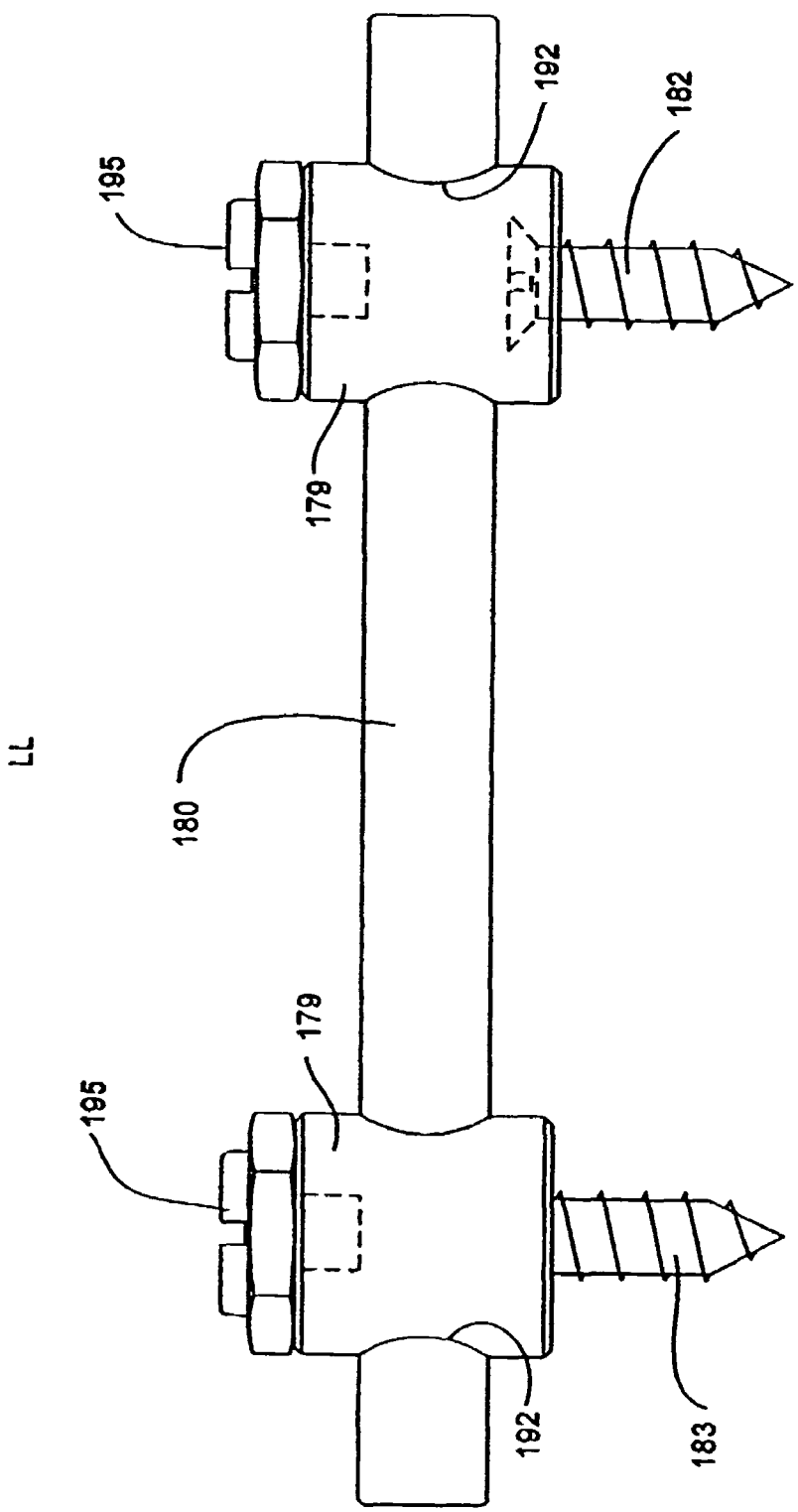
FIG. 16 is a side view of the embodiment of the spine stabilization system of the implant of the disclosed invention, depicted in FIG. 15.
Figure 17:
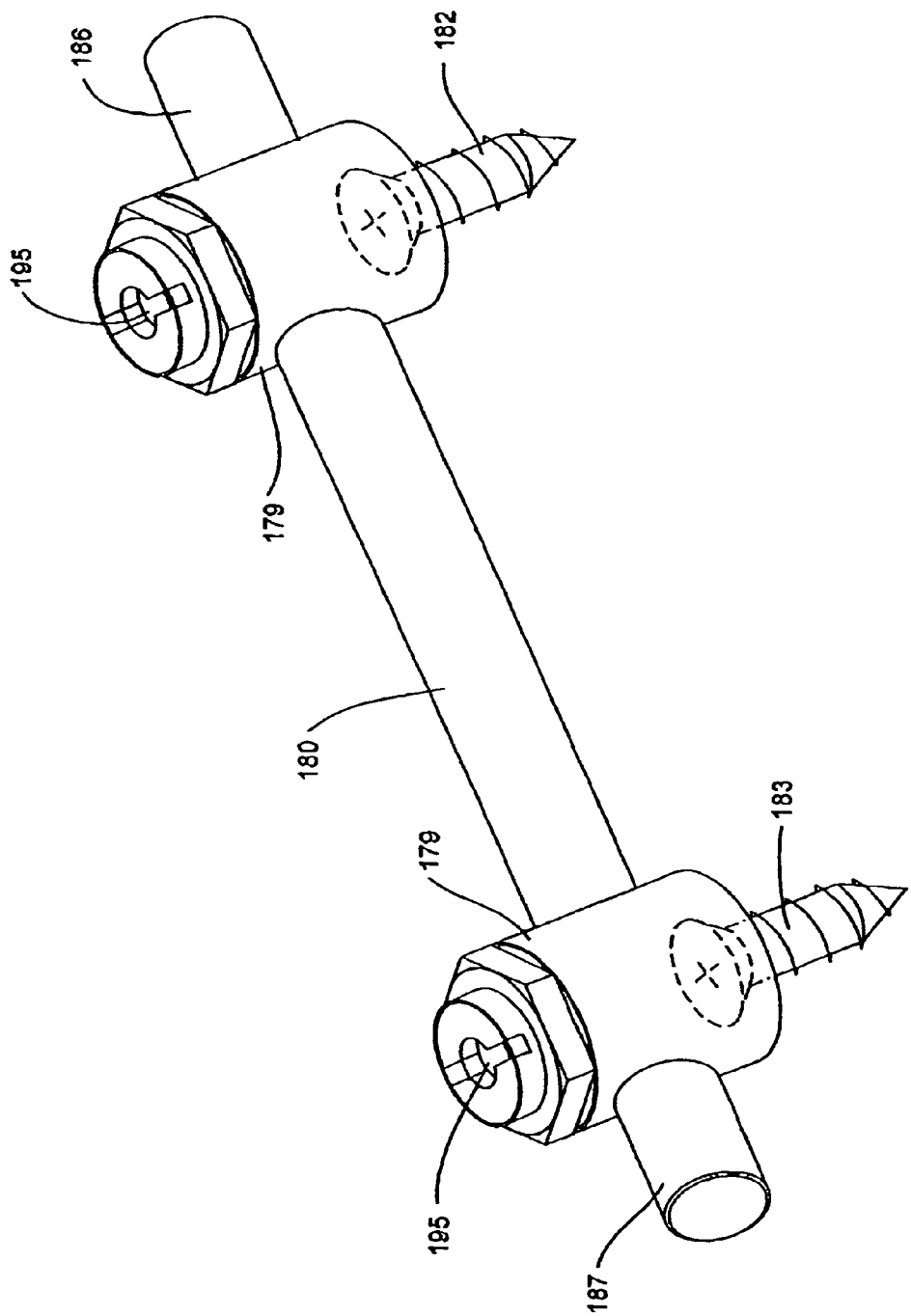
FIG. 17 is a perspective view of the embodiment of the spine stabilization system of the implant of the disclosed invention, depicted in FIGS. 15-16.
Figure 18:
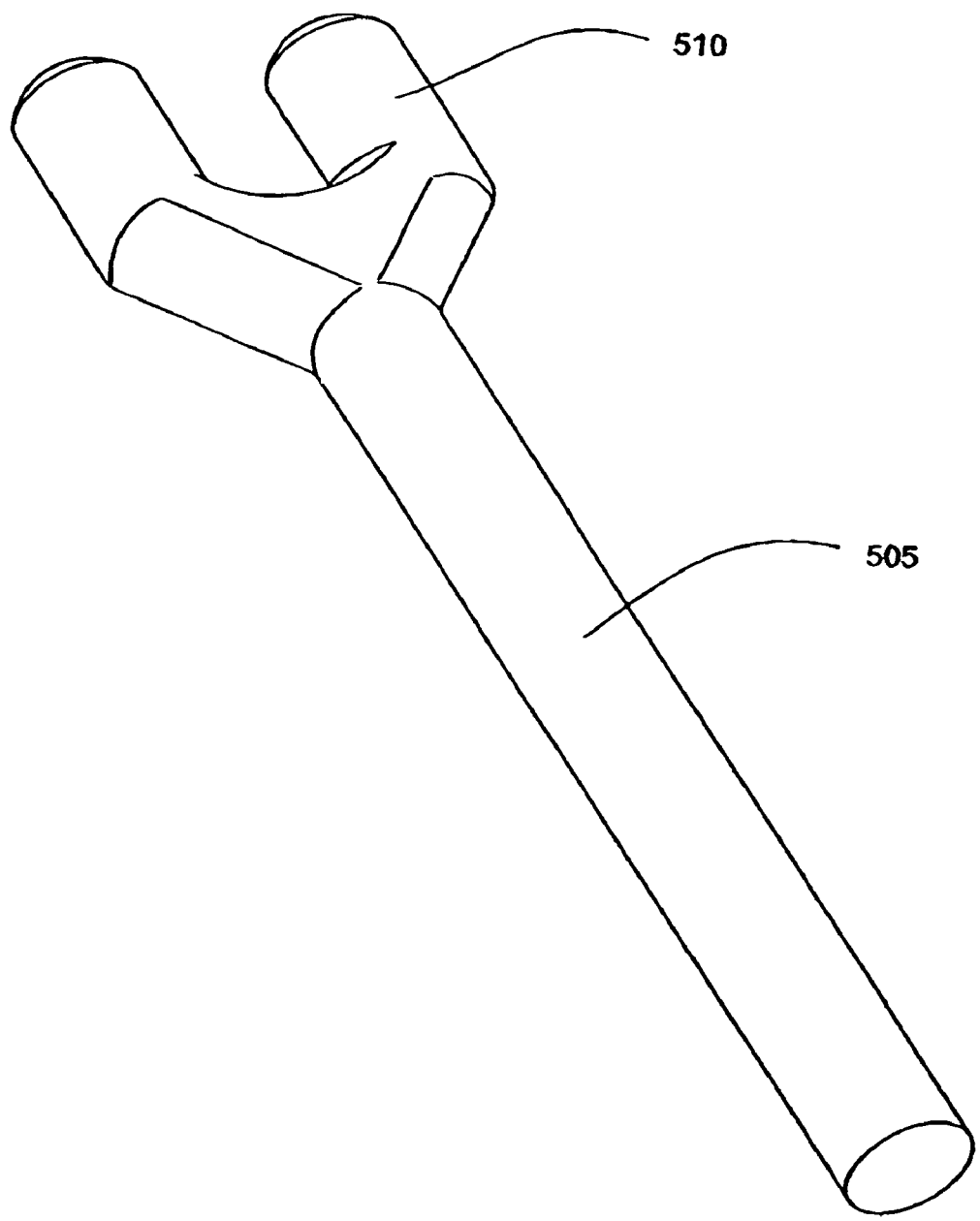
FIG. 18 is a perspective view of an embodiment of part of an insertion tool for implanting an embodiment of the implant of the disclosed invention.
Figure 19:
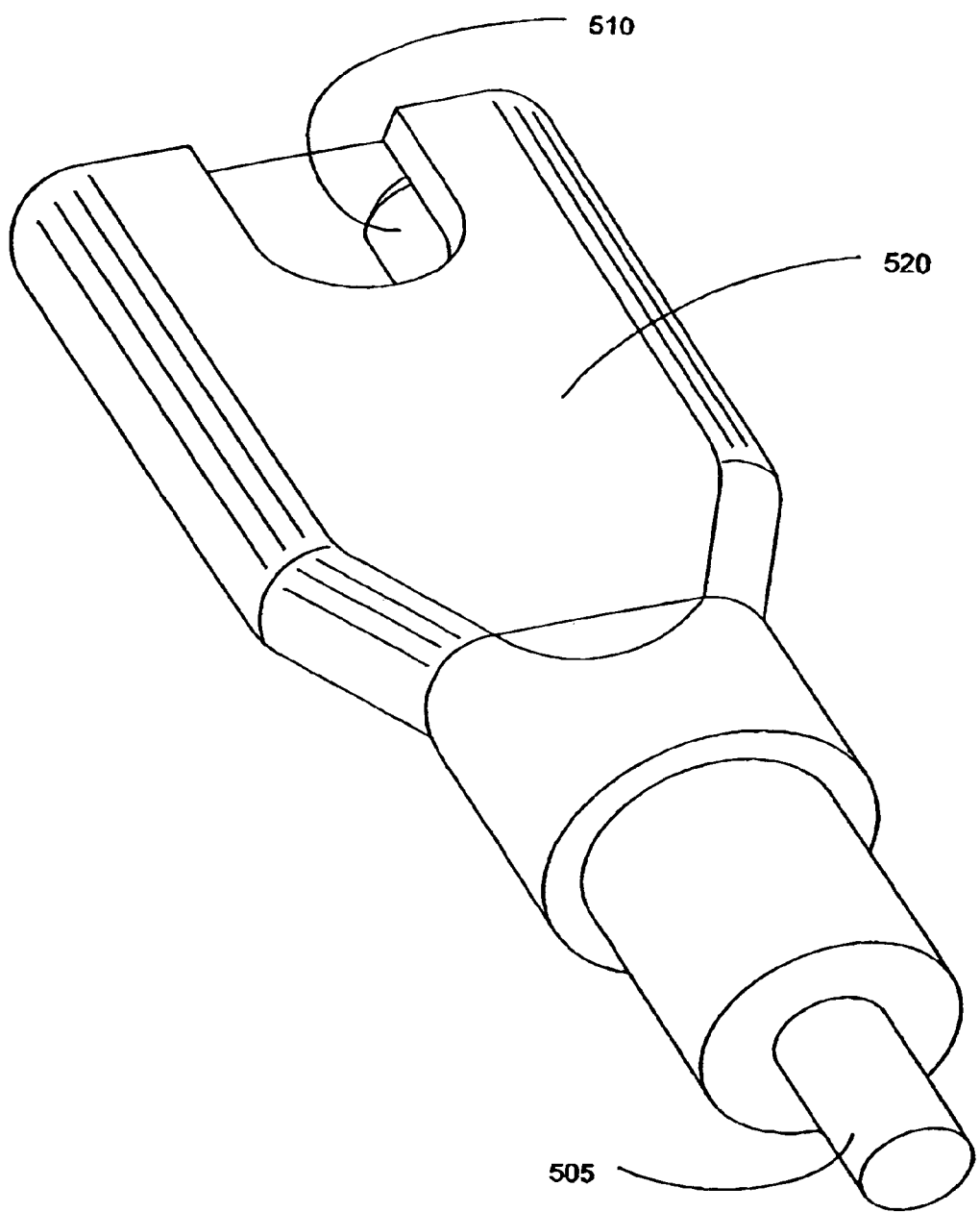
FIG. 19 is a perspective view of an embodiment of an additional part of an insertion tool for implanting an embodiment of an implant of the disclosed invention, in combination with the part depicted in FIG. 18.
Figure 20:
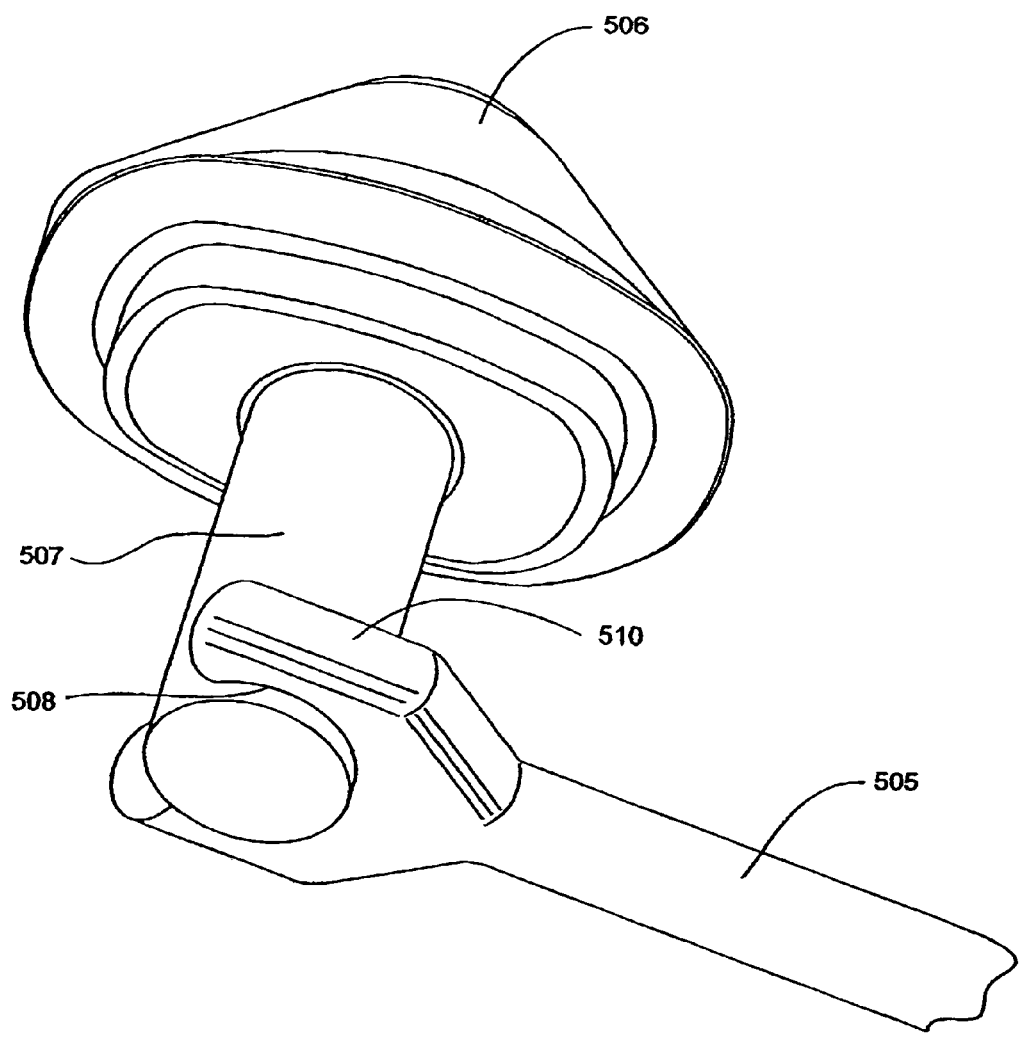
FIG. 20 is a perspective view of a further part of an embodiment of an insertion tool for implanting an embodiment of an implant of the disclosed invention.
Figure 21:
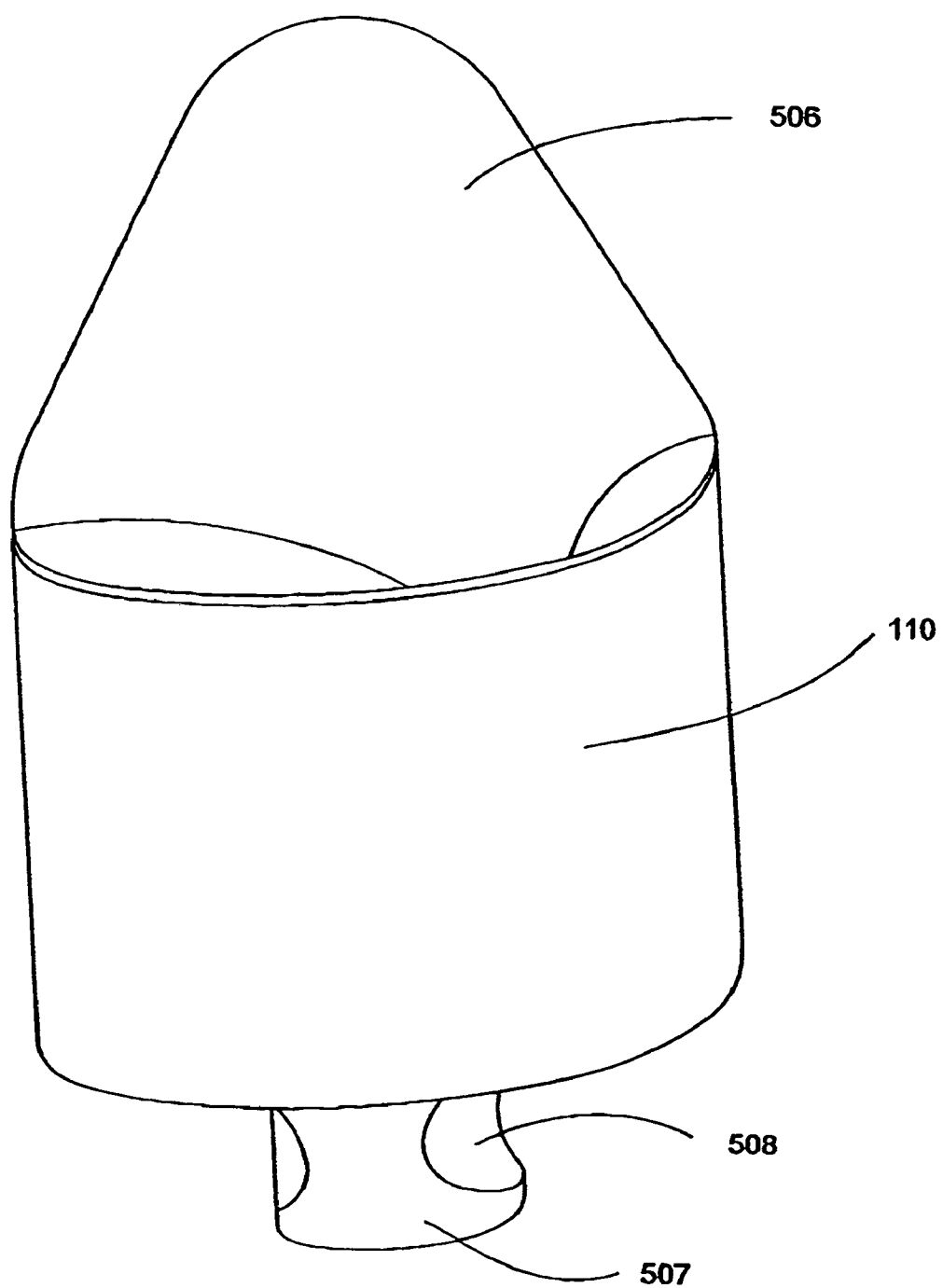
FIG. 21 is a perspective view of an additional part of an insertion tool for implanting an embodiment of an implant of the disclosed invention, in combination with the part depicted in FIG. 20.

As can be seen in FIG. 1, and as further depicted in FIGS. 16-18, the spine stabilization system can be a system incorporating appropriate bone anchors to anchor stabilization implants to the left lateral and right lateral sides of the spine. By way of example only, the implant can secure a rod on both the left lateral and right lateral sides of the spine. These elements, and in particular, the left lateral and right lateral rods, can serve as a scaffold system for securing the tethers emerging from the distraction body 105.

Pedicle screws 182, 183 can be used as bone anchors to anchor hubs 179 which will secure the rods 180, 181 with which the first tether 140 and second tether 165 respectively can connect to anchor the distraction body 105. Two pedicle screws 182, 183 anchor the hubs 179, for example, to the left lateral pedicles of two adjacent vertebrae. An upper left lateral pedicle receives an upper left pedicle screw 182, and a lower left lateral pedicle receives a lower left pedicle screw 183.

Two pedicle screws also anchor the other hubs 179 to the right lateral pedicles of the same two adjacent vertebrae. An upper right lateral pedicle receives an upper right pedicle screw and a lower right lateral pedicle receives a lower right pedicle screw.

The hubs 179 secured by the pedicle screws can secure a rod on each lateral side of the sagittal plane of the spine, with each rod oriented, for example, substantially parallel to the sagittal plane of the spine. The first rod 180 can pass through bores 192 through the hubs 179.

Each of the hubs 179 can receive a secondary screw 195. The secondary screw secures the rod 180 and prevents displacement. Alternatively, the hubs 179 can receive a snapping member to secure the rod or other cap or mechanism that serves to secure the rod 180 or other cap or mechanism serves to secure the rod 180

Once in place, the left or first rod 180 and the right or second rod 181 can be used to anchor the first and second tethers, as disclosed above or in equivalent fashion. Again, other stabilization systems known in the art can be used to anchor the tethers of the implant 100. It is also to be understood that other anchor mechanisms can be used that are not stabilization systems. For example, bone screws can be used to anchor the tethers of the implant 100 to appropriate structures of the spine.

In an alternative embodiment, depicted in FIGS. 12-15, the distraction body 205 of the implant 200 has a first wing 225 that is secured to or integral with the spacer 210, and a second wing 230 that is secured to or integral with spacer 210.

Moreover, in this embodiment, each wing 225, 230 of the implant 200 has only a bore. That is, the first wing 225 has a first bore 235, and the second wing 230 has a second bore 260. As it will be appreciated, in this embodiment, the first tether 240 and the second tether 265 do not pass through the spacer 210 in opposite directions, as in the other embodiments described. In contrast, the first tether 240 is anchored at a first end 245 to the first bore 235 of the first wing 225. The second end 250 of the first tether 240 is secured to the spine stabilization system on the same side on which the first end 245 is anchored to the first bore 235.

In similar fashion, the first end 270 of the second tether 265 is anchored to the second bore 260 of the second wing 230. The second end 275 is secured to the spine stabilization system on the same side on which the first end 270 is anchored to the second bore 260.

As set forth above, the second ends 250, 275 of the first and second tethers 240, 265 respectively, anchor the tethers to the spine stabilization system. The second ends 250, 275 can be wrapped around the rods 280, 281 of the spine stabilization system. The first and second tethers 240, 265 can be secured to the spine stabilization system with a cuff 278 made from a biocompatible material that is capable of grasping the tether material and preventing it from slipping. Alternatively, the tethers 240, 265 can be sewn, pierced, pinned, or tied, to secure the tethers to the spine stabilization system. The configuration of the distraction body 205 tethered to the spine stabilization system prevents displacement of the distraction body 205 from the position between the adjacent spinous processes. The combination of the spine stabilization system with spine distraction provides an improved therapeutic benefit to the patient receiving such implant.

The disclosed invention further includes a method 400 for implanting the interspinous implant with stabilization system. The steps for implanting implant 100 will be described, but one of ordinary skill in the art will appreciate that implant 200 also can be implanted in a similar manner.

The spinous processes are preferably accessed from the sides, in order not to alter and to leave the spinal ligaments in place, including but not limited to the superspinous ligament. The spine is prepared (Steps 400, 410) for implantation by making an incision and accessing the affected vertebrae. Pedicle screws, step 420, or other appropriate bone anchors are installed, for example, in the pedicles of an upper and a lower affected vertebra, to anchor the hubs 179 needed for sustaining the left/first rod 180 and the right/second rod 181. Secondary screws 195 are applied to secure the rods 180, 181 in position.

The distraction body 105 then is inserted laterally, step 430, and positioned, step 440, between the spinous processes of the two adjacent affected vertebrae. The first tether 140 and the second tether 165 can then be configured to anchor the distraction body to the spine stabilization system, step 450. The distraction body 105 of the implant 100 can already have the first tether 140 and the second tether 165 prepared to anchor the distraction body 105 to the left/first rod 180 and the right/second rod 181, as disclosed above. The implant 100 can have the second end 175 of the second tether 165 exiting from the first inner bore 155, ready to anchor to the left/first rod 180, and the second end 150 of the first tether 140 exiting from the second inner bore 176, ready to anchor to the right/second rod 181.

Implant 200, in contrast, will have the first tether 240 secured to the left/first rod 280, and the second tether 265 secured to the right/second rod 281 (step 450).

An alternative implantation method can use the implantation tool depicted in FIGS. 18-22. The implantation tool 500 can be used to assemble the implant 100 as it is being implanted. The implantation tool 500 can comprise a holding rod 505 that can have a mating end 510 that mates with a part of a tissue expander 506 of the implant and that holds the spacer 110 while it is being positioned between adjacent spinous processes. The mating end 510 can be in the shape of a fork with two prongs, by way of example.

The holding rod 505 can be housed inside a housing unit 520 which is slidable on the holding rod 505 in order to capture the tissue expander 506. The housing unit 520 allows the mating end 510 of the holding rod 505 to retain the tissue expander 506 when a groove 508 in the shaft 507 of the tissue expander 506 is received by the forks of the mating end 510.

Figure 5:
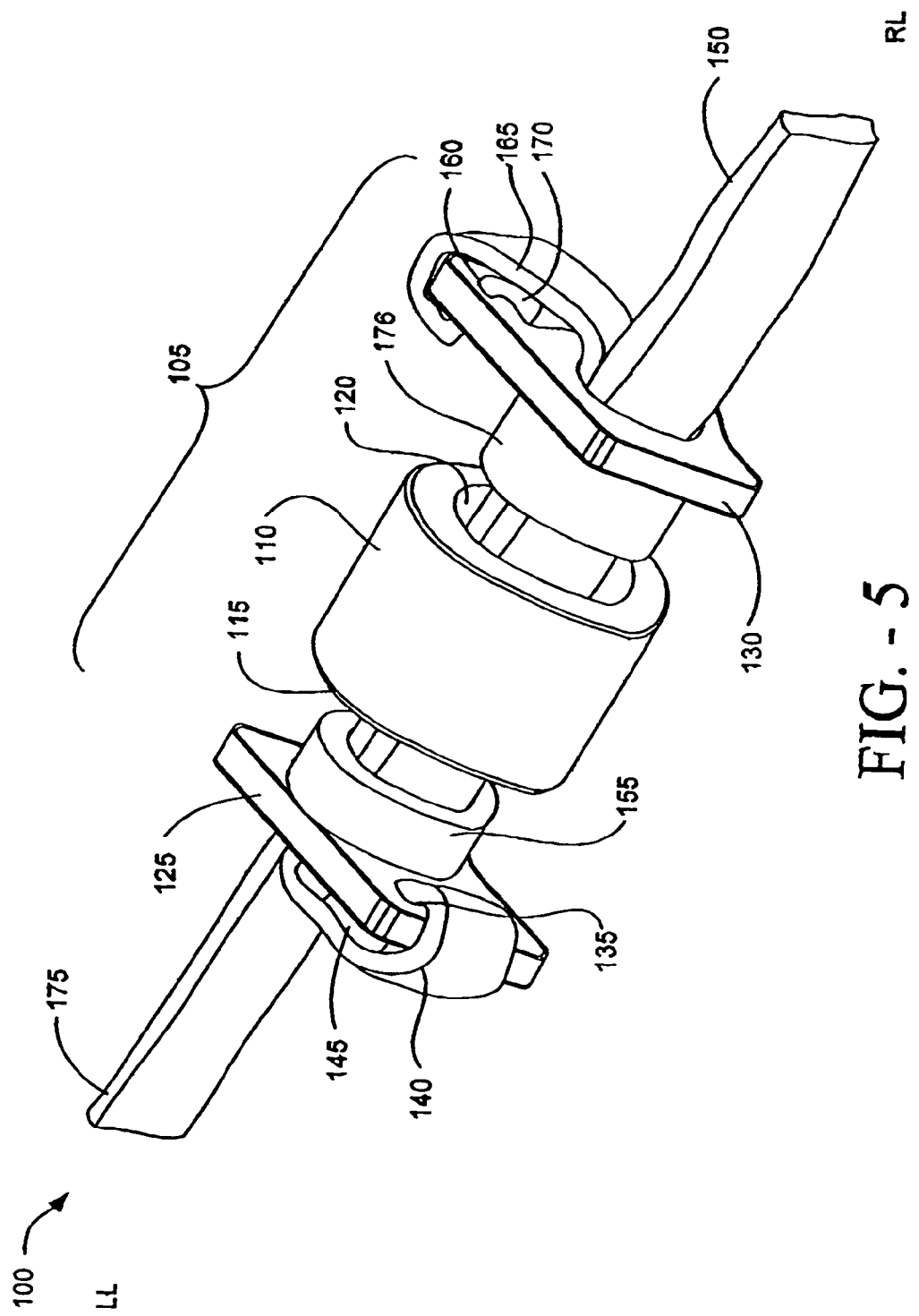
FIG. 5 is an exploded perspective view of the embodiment of the distraction body of an implant of the disclosed invention depicted in FIGS. 1-4, with tethers.
Figure 6:
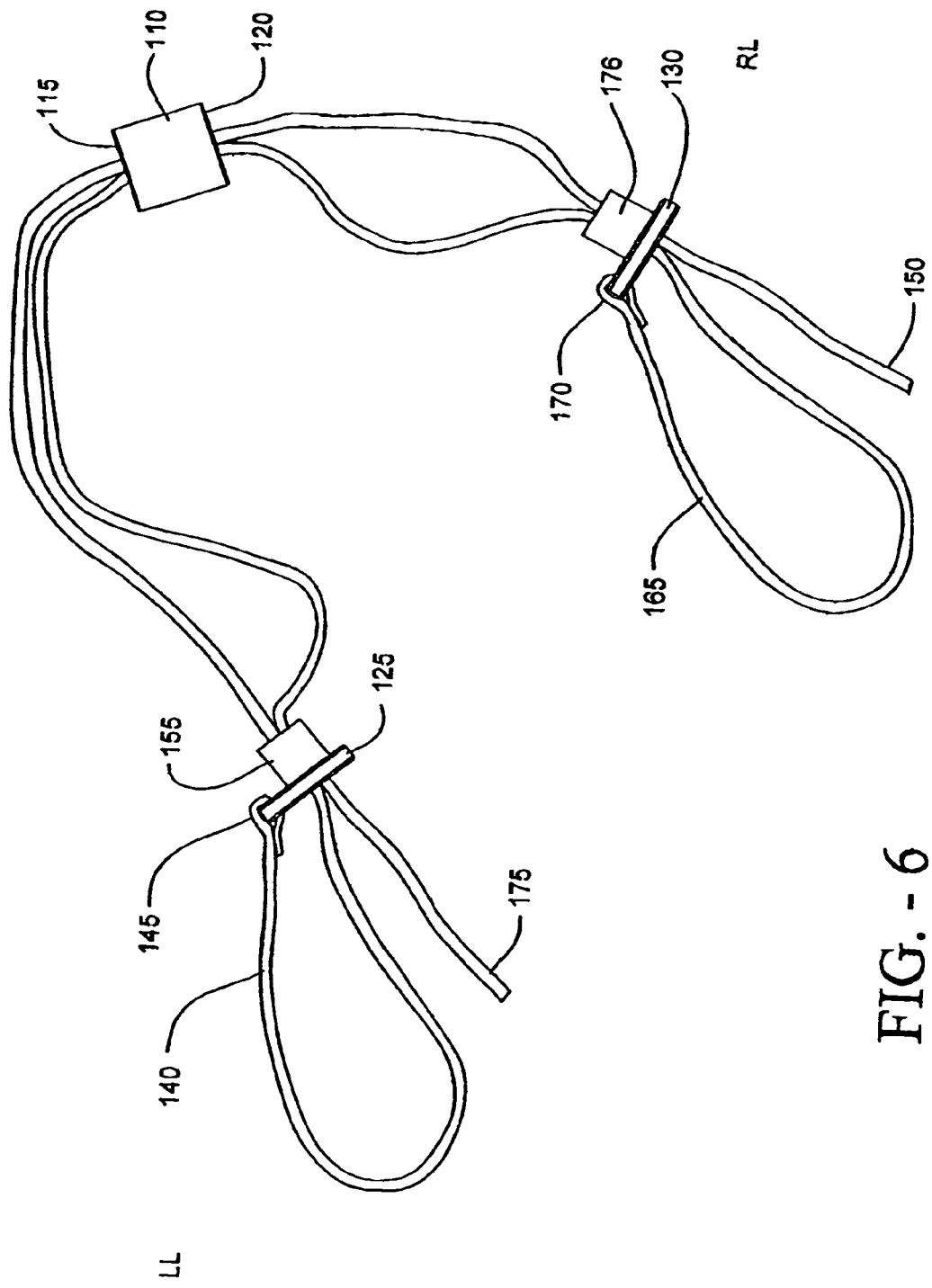
FIG. 6 is a further exploded side view of the embodiment of the distraction body of an implant of the disclosed invention depicted in FIGS. 1-5, with tethers.
Figure 7:
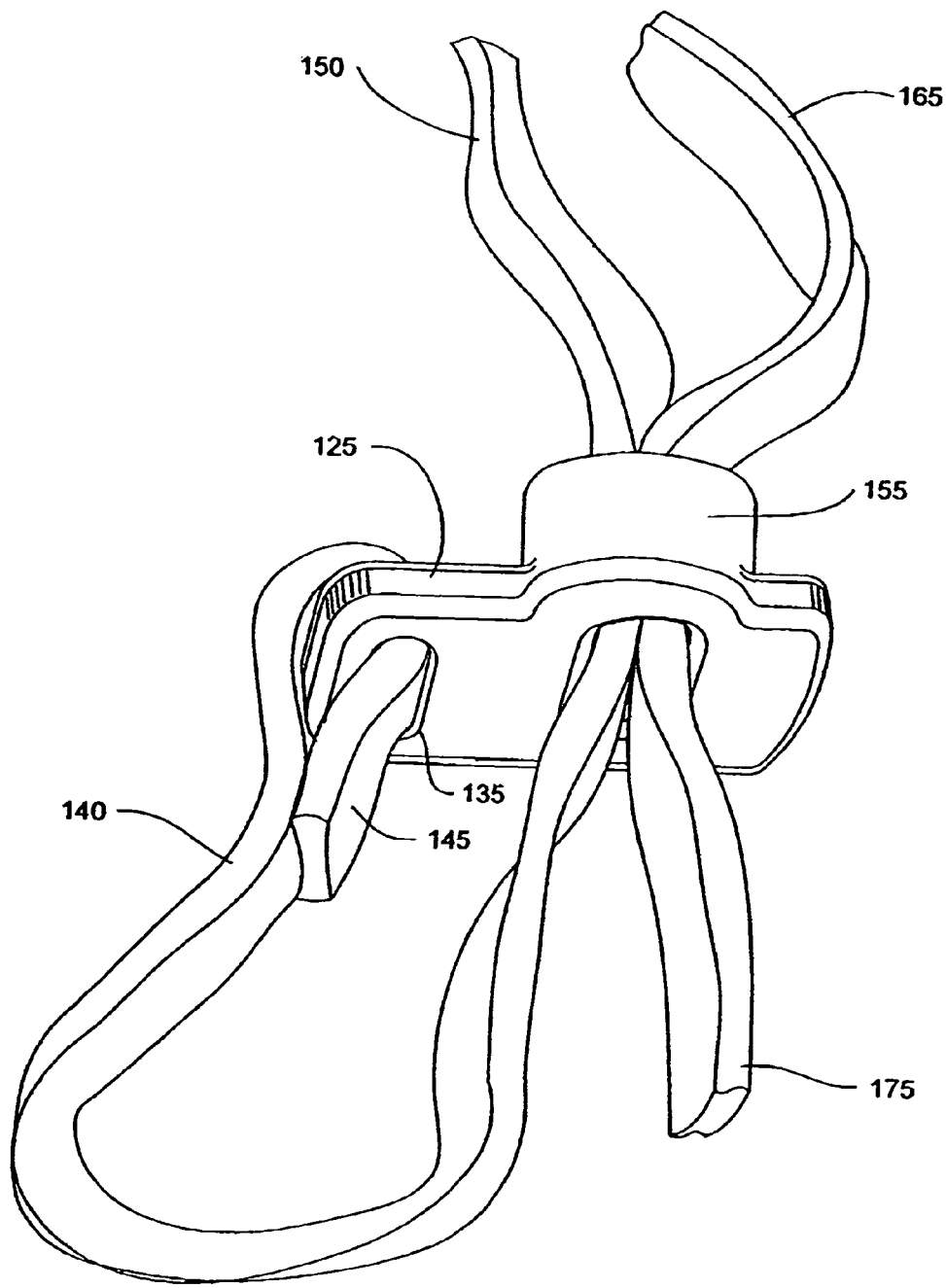
FIG. 7 is an end view of an embodiment of a wing of the distraction body of the implant of the disclosed invention depicted in FIGS. 1-6, with a tether threaded through and anchored to the wing.
Figure 8:
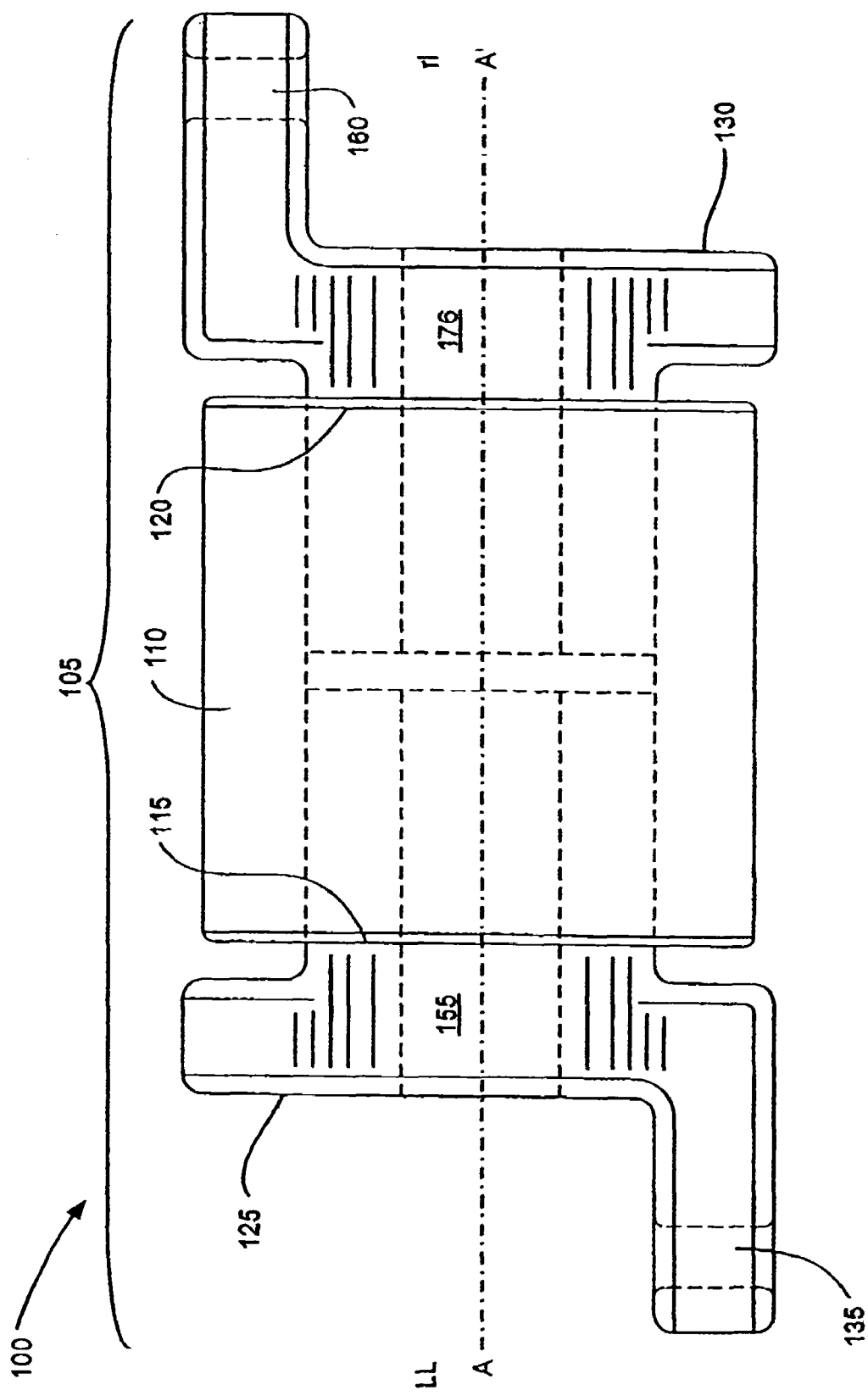
FIG. 8 is a side view of an alternative embodiment of the distraction body of an implant of the disclosed invention.
Figure 9:
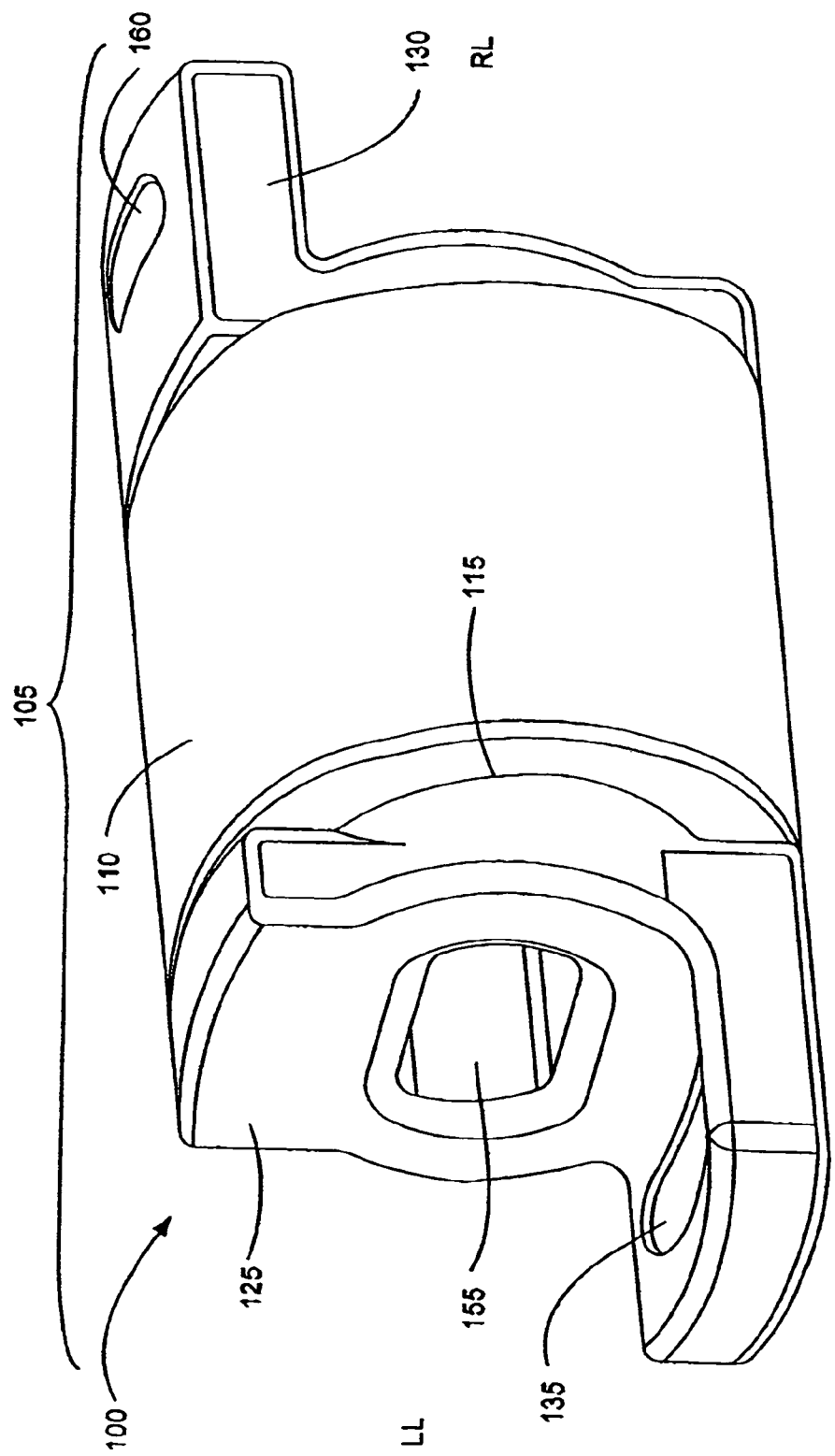
FIG. 9 is a perspective view of the embodiment of the distraction body of an implant of the disclosed invention depicted in FIG. 8.
Figure 10:
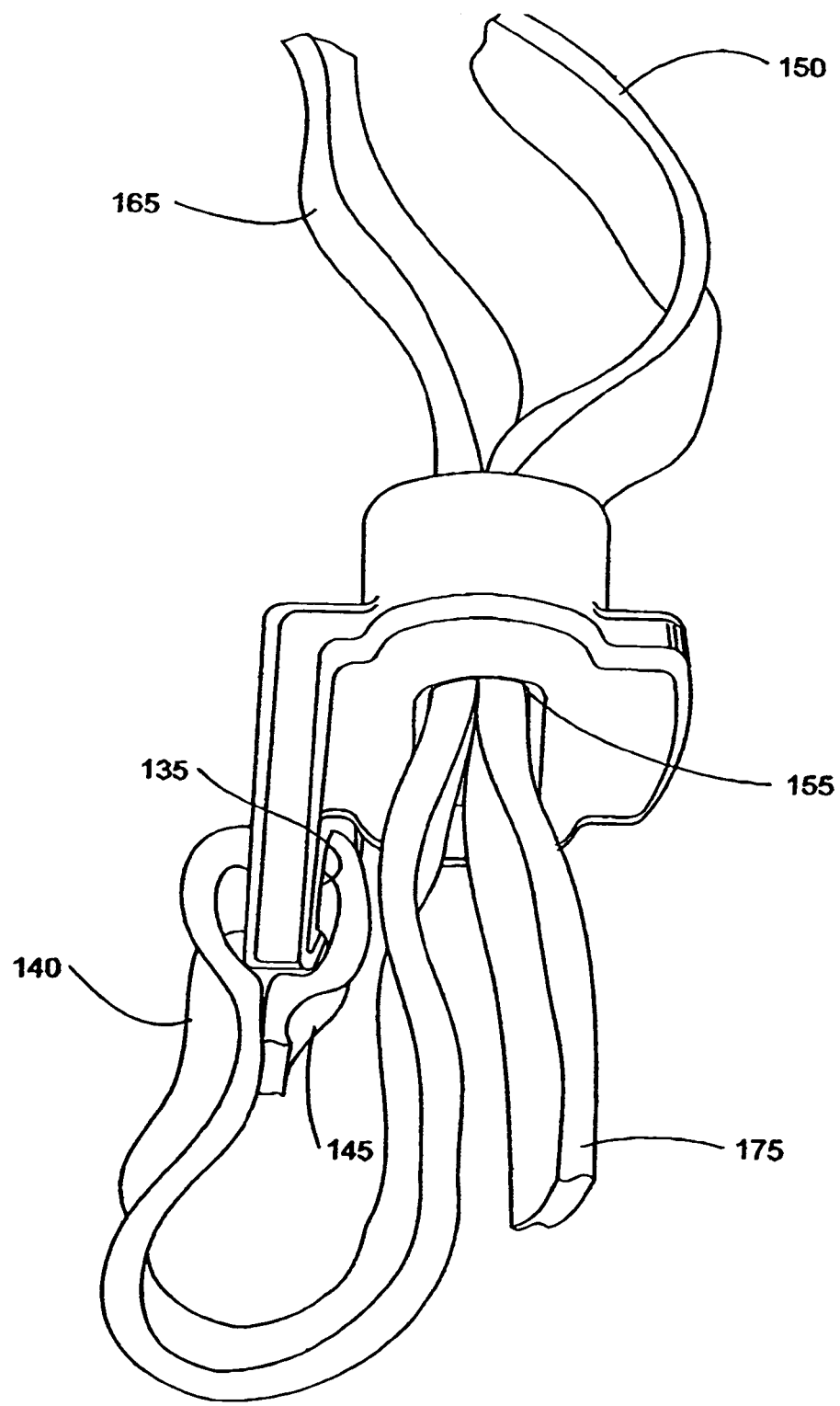
FIG. 10 is an end view of a wing of the embodiment of the distraction body of an implant of the disclosed invention depicted in FIGS. 8 and 9, with a first end of a first tether anchored to the wing and a second end of a second tether threaded through the wing.
Figure 11:
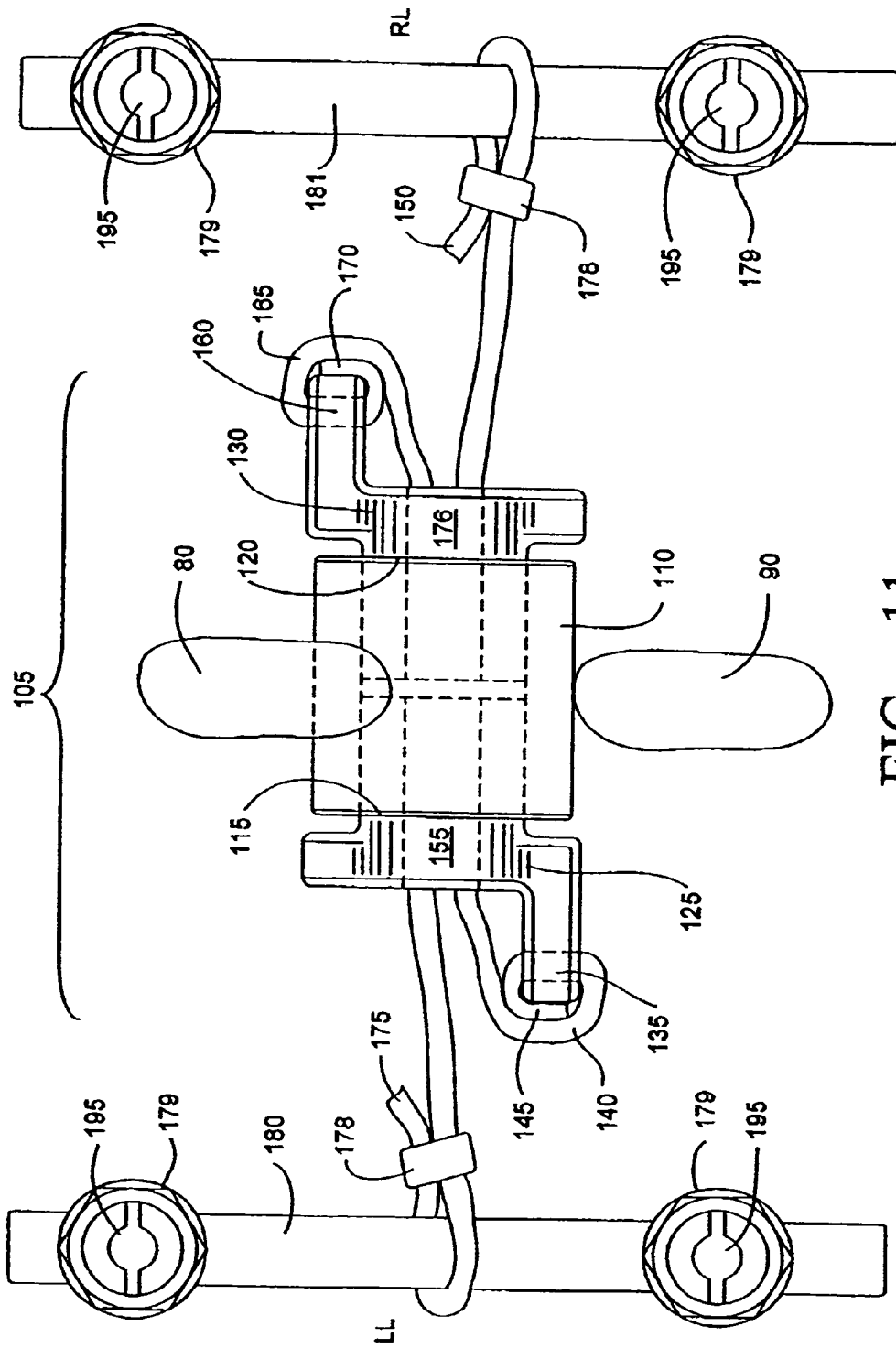
FIG. 11 is a posterior view of the embodiment of the disclosed invention depicted in FIGS. 8-10, depicted here as implanted between spinous processes of adjacent affected vertebrae.
Figure 22:
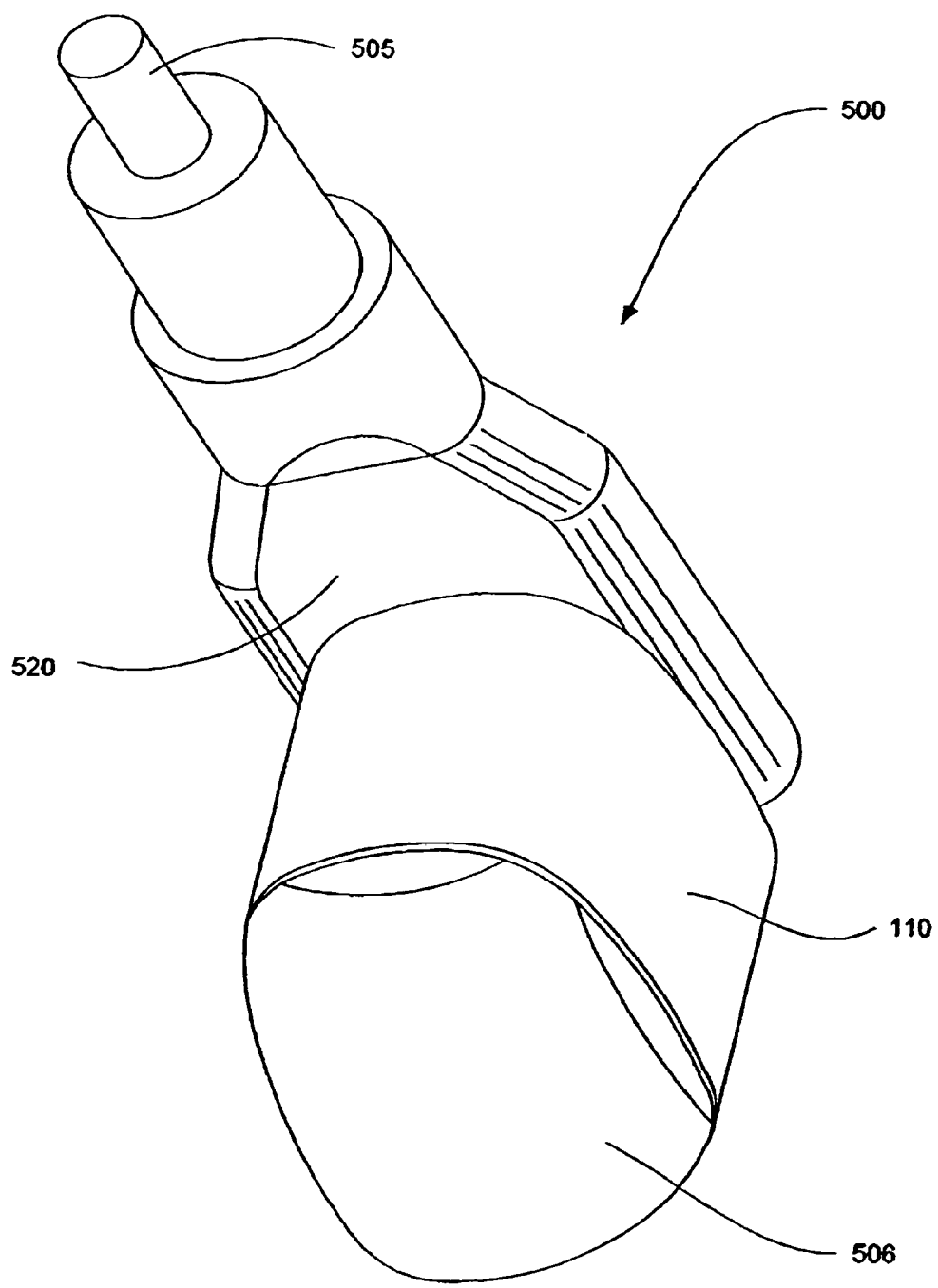
FIG. 22 is a perspective view of a fully-assembled insertion tool for implanting an embodiment of an implant of the disclosed invention.
Figure 23:
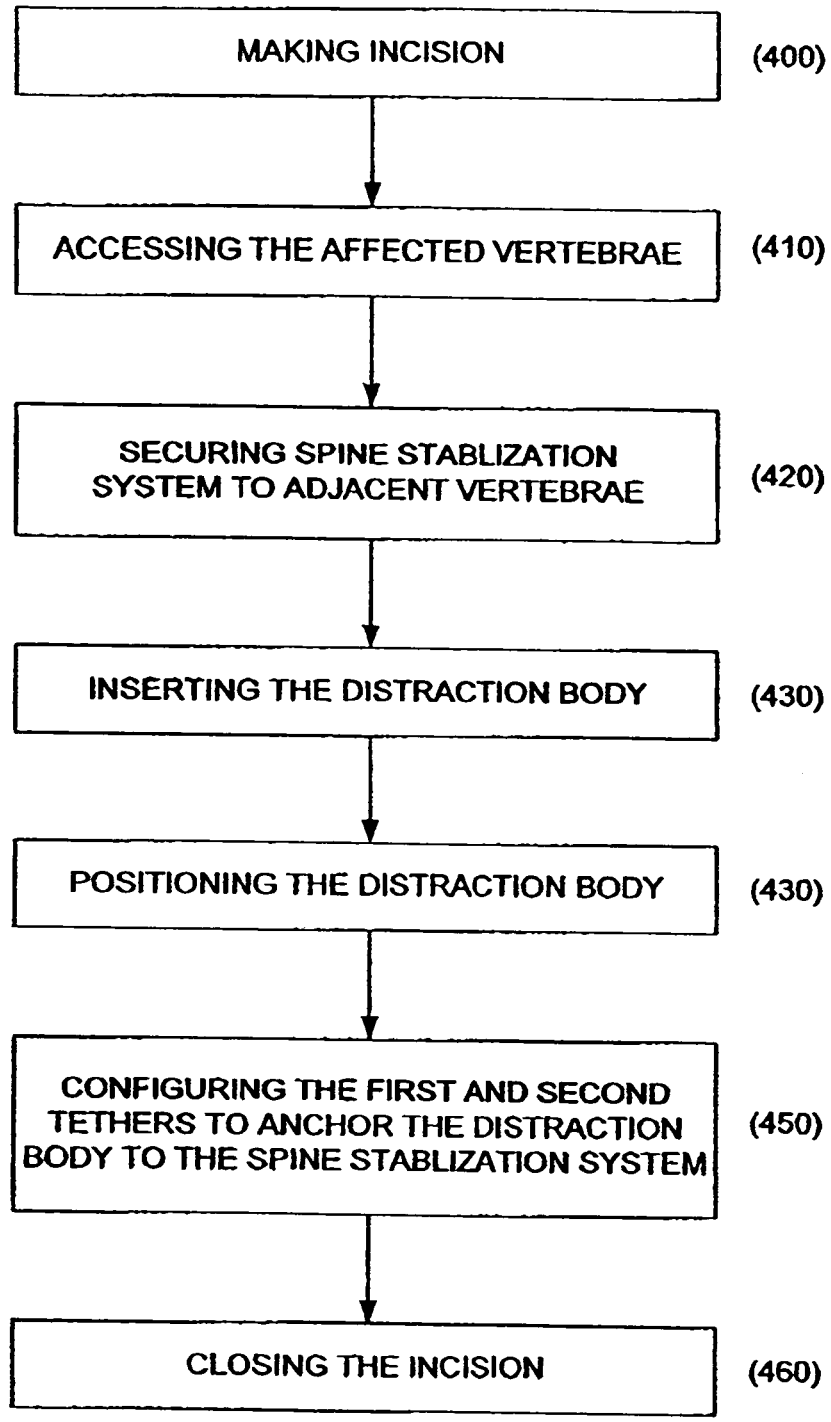
FIG. 23 is a flow chart depicting an embodiment of the method of the invention.

As can be seen in the assembled view in FIG. 22, the tool 500 is used to hold the spacer 110 and insert the spacer 110 laterally between the spinous processes. The tissue expander 506 can urge the tissue apart without severing the ligaments and also distract the adjacent spinous processes. Once the spacer 110 is positioned between the spinous processes, the tool 500 with the tissue expander 506 can be removed leaving the spacer 110 in place. With the spacer 110 in place, the implant 100 can be assembled in place. That is to say that the tethers which are preassembled onto the first and second wings are threaded through the spacer and the other respective wings much as seen in FIGS. 5, 6 and 7. The implant then is fitted together as seen in FIG. 1. After that assembly, the tethers can be secured to the stabilization system also as seen in FIG. 1. The implant 100 as seen in FIGS. 8, 9, 10, and 11 can be assembled and implanted in a similar manner.

Figure 12:
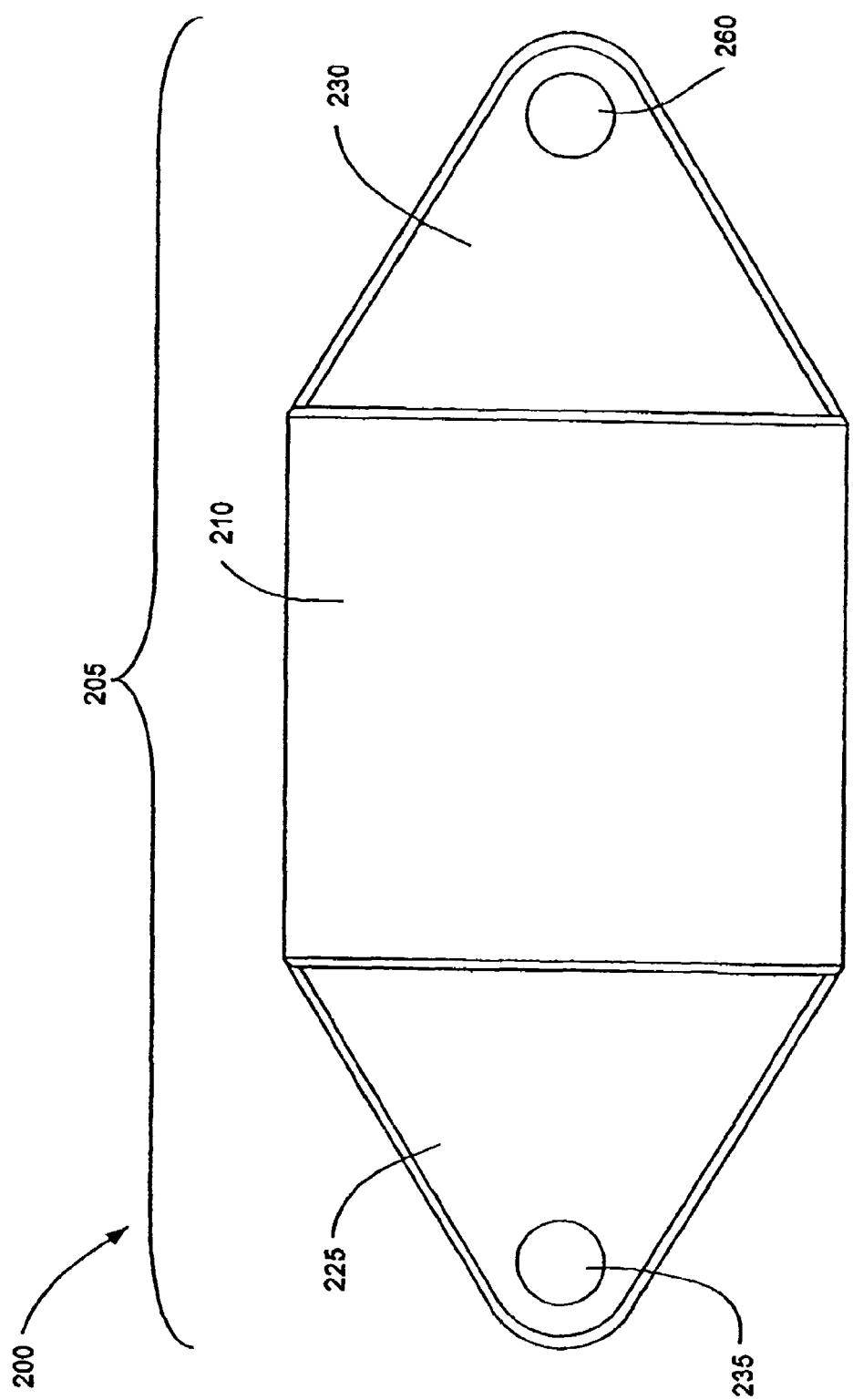
FIG. 12 is a side view of a further embodiment of the distraction body of the implant of the disclosed invention.
Figure 13:
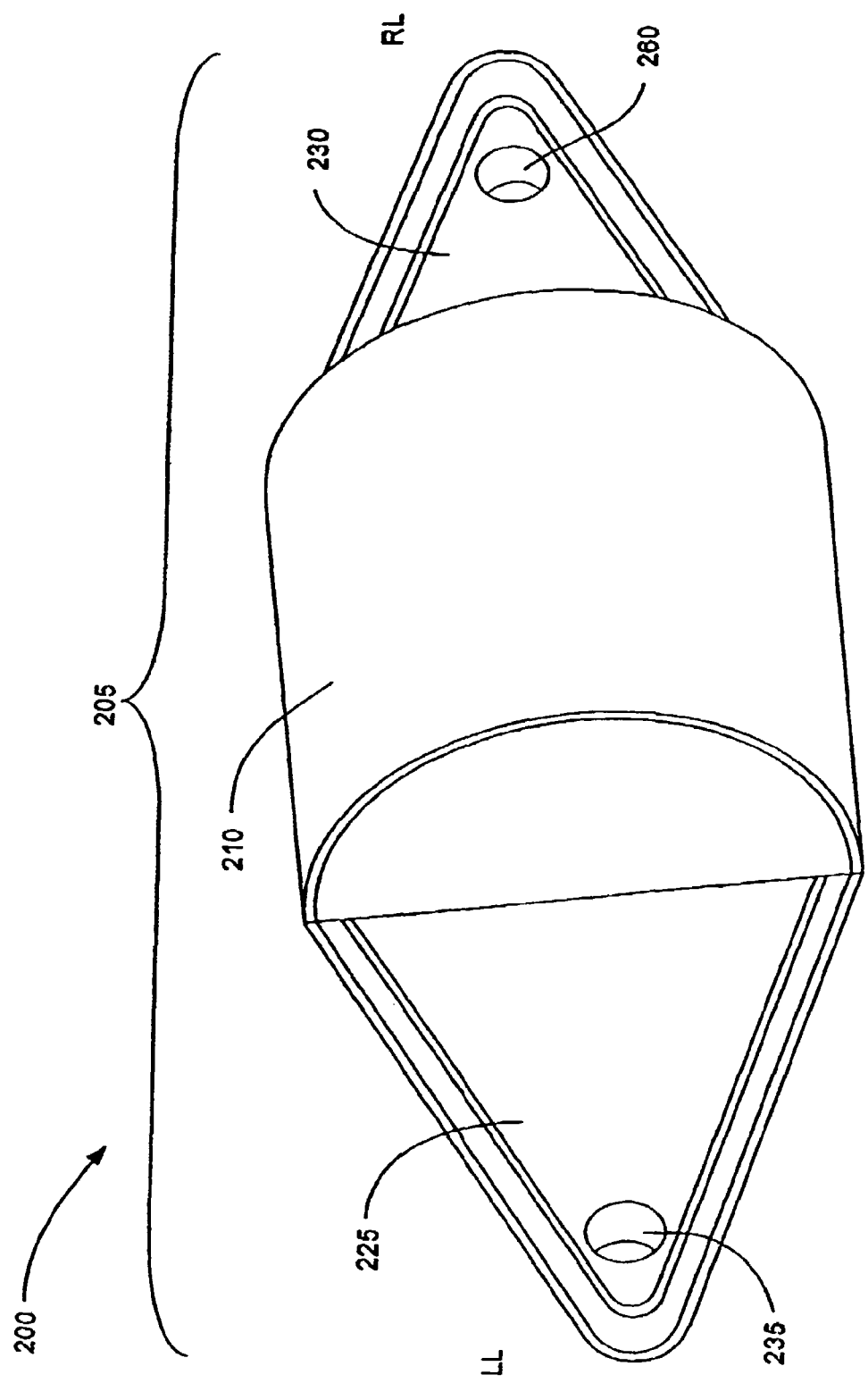
FIG. 13 is a perspective view of the embodiment of the implant of the disclosed invention depicted in FIG. 12.
Figure 14:
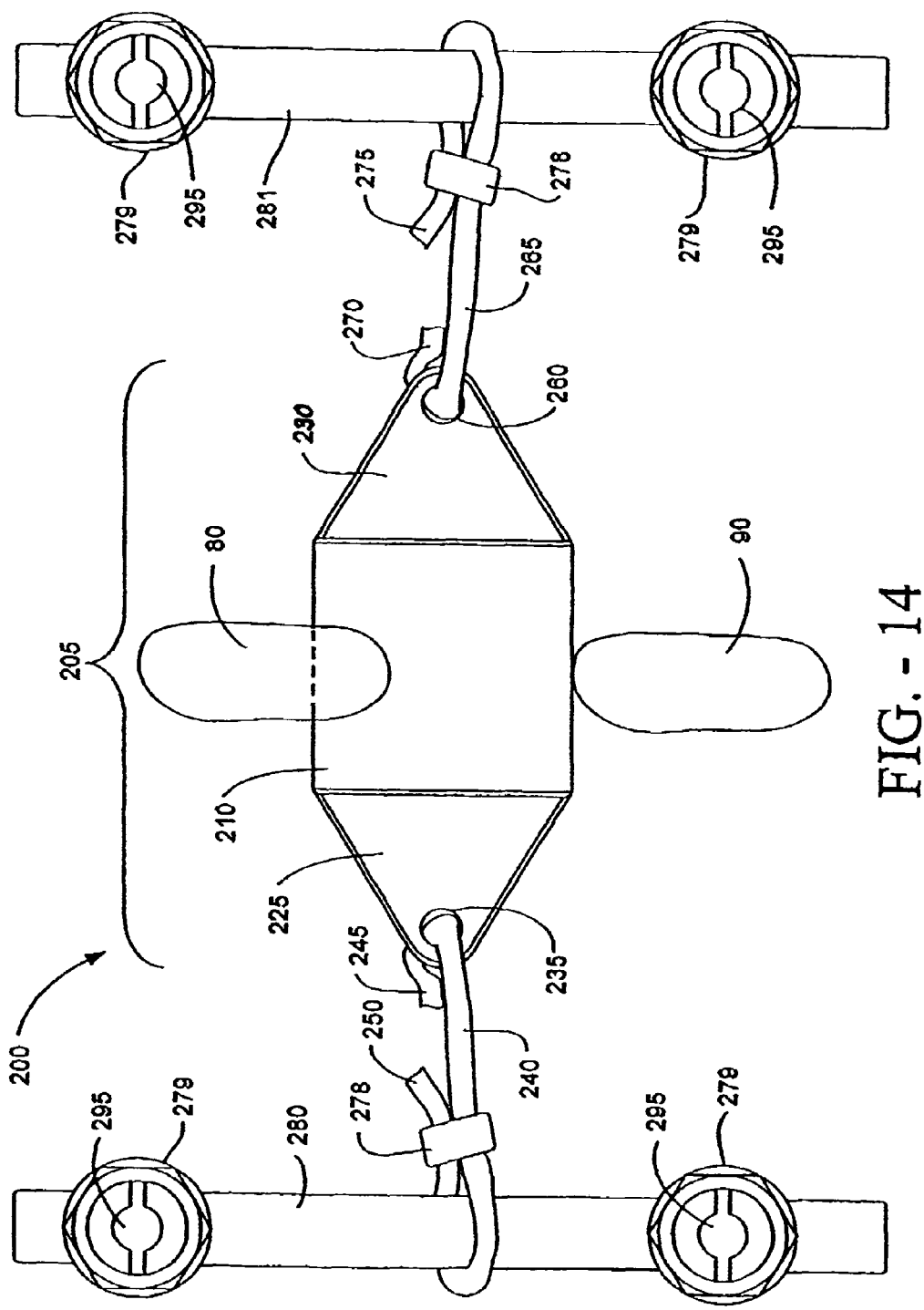
FIG. 14 is a posterior view of the embodiment of the implant of the disclosed invention depicted in FIGS. 12-13, depicted here as implanted between the spinous processes of adjacent affected vertebrae.
Figure 15:
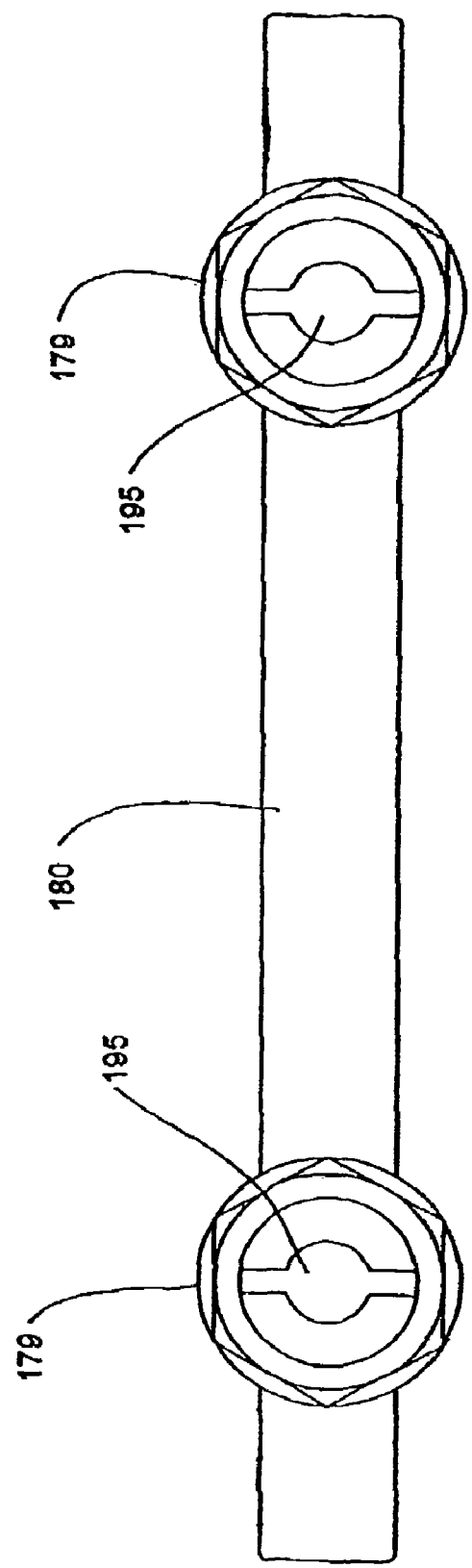
FIG. 15 is a posterior view of an embodiment of the spine stabilization system of the implant of the disclosed invention, without tethers.

With respect to the implant 200 of FIGS. 12, 13, and 14, the spacer 210 can be urged laterally between the spinous processes until the first wing emerges from the opposite side of the spinous processes. If desired, the tethers can be preassembled to the spacer 210 and thus the tether 240 can be used to help guide and urge the spacer 210 between the spinous processes. Once the spacer is positioned, the tethers can be secured to the stabilization system.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

What is claimed:

1. A first implant to maintain distraction of adjacent spinous processes of a patient and which is adapted to be secured to a second spine implant, the first implant comprising:
   a spacer body adapted to be positioned between the adjacent spinous processes, the spacer body having a first end and a second end with an axis extending therebetween, the spacer body receivable between the spinous processes for compression thereby during extension between the spinous processes with the axis disposed generally transverse to the spinous processes; wherein the spacer body includes a first open end and a second open end;
   a first tether secured to the spacer so as to extend axially from the first end;
   a second tether secured to the spacer so as to extend axially from the second end, the first and second tethers each adapted to secure the spacer to the second spine implant so as to inhibit movement of the spacer from between the spinous processes;
   a first wing which fits into the first open end and anchors the first tether;
   a second wing which fits into the second open end and anchors the second tether;
   wherein the first wing includes:
      a first inner bore adapted to be positioned inside the first open end of the spacer body;
      a first outer bore adapted to be positioned outside the first open end of the spacer body;
   wherein the second wing includes:
      a second inner bore adapted to be positioned inside the second open end of the spacer body; and
      a second outer bore adapted to be positioned outside the second open end of the spacer body.

2. The first implant of claim 1, wherein:
   the first tether is adapted to be anchored at a first end to the first outer bore and threaded from a second end through the first inner bore, through the spacer body in a first direction, through the second inner bore, and through the second open end of the spacer body and secured to a first component of the second spine implant at the second end of the first tether; and the second tether is anchored at a first end to the second outer bore and threaded from a second end through the second inner bore, through the spacer body in a second direction opposing the first direction of the first tether, through the first inner bore, and through the first open end of the spacer body and secured to a second component of the second spine implant at the second end of the second tether.

3. The first implant of claim 2, wherein the first tether is secured to the first component of the second spine implant by a cuff made of a biocompatible material, and the second tether is secured to the second component of the second spine implant by another cuff made of the biocompatible material.

4. The first inplant of claim 2, wherein the first tether is secured to the first component of the second spine implant by sutures, and the second tether is secured to the second component of the second spine implant by sutures.

5. The first implant of claim 1, wherein the first outer bore is bent at an angle from the first inner bore; and the second outer bore is bent at the angle from the second outer bore.

6. The implant of claim 1, wherein said first and second wings are about perpendicular to the spacer body.

7. The implant of claim 1, wherein said first and second wings are about parallel to the spacer body.

* * * * *